US007889833B2

(12) United States Patent
Hagiwara

(10) Patent No.: US 7,889,833 B2
(45) Date of Patent: Feb. 15, 2011

(54) X-RAY TOMOGRAPHY APPARATUS AND ARTIFACT REDUCING METHOD

(75) Inventor: Akira Hagiwara, Tokyo (JP)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 620 days.

(21) Appl. No.: 11/924,462

(22) Filed: Oct. 25, 2007

(65) Prior Publication Data

US 2008/0130823 A1     Jun. 5, 2008

(30) Foreign Application Priority Data

Oct. 27, 2006    (JP) .............................. 2006-292156

(51) Int. Cl.
*A61B 6/03* (2006.01)
(52) U.S. Cl. .......................................................... 378/4
(58) Field of Classification Search ...................... 378/4; 382/128–131, 275
See application file for complete search history.

(56) References Cited

U.S. PATENT DOCUMENTS

| | | | |
|---|---|---|---|
| 5,537,485 | A | 7/1996 | Nishikawa et al. |
| 5,712,889 | A | 1/1998 | Lanzara et al. |
| 5,828,725 | A | 10/1998 | Levinson |
| 6,373,920 | B1 | 4/2002 | Hsieh |
| 6,463,118 | B2 | 10/2002 | Besson |
| 7,359,476 | B2 | 4/2008 | Hagiwara |
| 2005/0053187 | A1 | 3/2005 | Hagiwara |
| 2005/0226365 | A1 | 10/2005 | Taguchi |
| 2006/0029285 | A1 | 2/2006 | Hein et al. |

(Continued)

FOREIGN PATENT DOCUMENTS

EP         0962888 A2     12/1999

(Continued)

OTHER PUBLICATIONS

Kachelriess et al., Improving PET/CT Attenuation Correction with an Iterative CT Beam Hardening Correction, 2005, 2005 IEEE Nuclear Science Symposium Conference Record, pp. 1905-1909.*

(Continued)

*Primary Examiner*—Edward J Glick
*Assistant Examiner*—John M Corbett
(74) *Attorney, Agent, or Firm*—Armstrong Teasdale LLP

(57) ABSTRACT

The present invention provides an X-ray tomography apparatus that reduces artifacts. The X-ray tomography apparatus includes scan device for exposing X rays to a subject to create projection data of the subject, CT value change specifying device for specifying the amount of change in CT value in a body-axis direction with respect to a target pixel of a tomographic image obtained by backprojecting the projection data, a first artifact determination unit for determining whether the amount of change in CT value is contained within a predetermined range in a peripheral decision pixel area containing the target pixel, a second artifact determination unit for determining that when the number of pixels contained in the predetermined range is found to be a first threshold value or more by a first artifact decision, the target pixel is as an artifact, and an artifact reduction unit for, when it is judged by the second artifact determination unit that the target pixel is as the artifact, performing image processing so as to reduce the artifact.

17 Claims, 15 Drawing Sheets

U.S. PATENT DOCUMENTS

2006/0285737 A1* 12/2006 Hamill et al. ............... 382/131
2007/0195931 A1* 8/2007 Ohishi ....................... 378/98.2
2008/0118022 A1 5/2008 Hagiwara

FOREIGN PATENT DOCUMENTS

JP 2003-325502 11/2003
JP 2005080918 3/2005

OTHER PUBLICATIONS

International Search Report, NL 1034578, dated Nov. 11, 2008, pp. 20.
Laurence Keselbrener et al., Nonlinear filters applied on computerized axial tomography: Theory and phantom images, Medical Physics, Jul. 1, 1992, pp. 1057-1064.
Xiangyang Tang et al., Cone beam volume CT image artifacts caused by defective cells in x-ray flat panel imagers and the artifact removal using a wavelet-analysis-based algorithm, Medical Physics, May 1, 2001, pp. 812-825.
Gary A. Mastin, Adaptive Filters for Digital Image Noise Smoothing: An Evaluation, Computer Vision Graphics and Image Processing, Academic Press, Jul. 1, 1985, pp. 103-121.
Roland T. Chin, et al., Quantitative Evaluation of Some Edge-Preserving Noise-Smoothing Techniques, Computer Vision Graphics and Image Processing, Academic Press, Jul. 1, 1983, pp. 67-91.
Marc Kachelriess et al., Generalized multi-dimensional adaptive filtering for conventional and spiral single-slice, multi-slice, and cone-beam CT, Medical Physics, Apr. 1, 2001, pp. 475-490.
Jiang Hsieh, Adaptive Interpolation Approach for Multi-slice Helical CT Reconstruction, Proceedings of the Spie—The International Society for Optical Engineering, May 1, 2003, pp. 8, vol. 5032.
Silver et al., Windmill Artifact in Multi-slice Helical CT, Proceedings of the Spie—The International Society for Optical Engineering, Feb. 17, 2003, pp. 10, vol. 5032.
Pitas et al., Nonlinear Digital Filters, 9.7—Two-component Image Filtering, Nonlinear Digital Filters: Principles and Applications, Dordrecht: Kluwer Academic Publishers, Jan. 1, 1990, pp. 284-290.
International Search Report, NL1034577, dated Nov. 18, 2008, pp. 15.

* cited by examiner

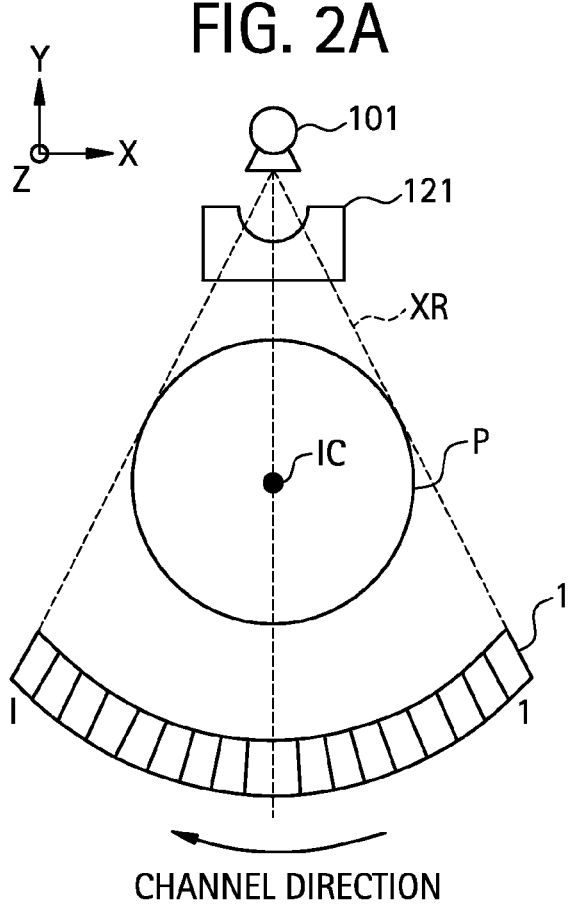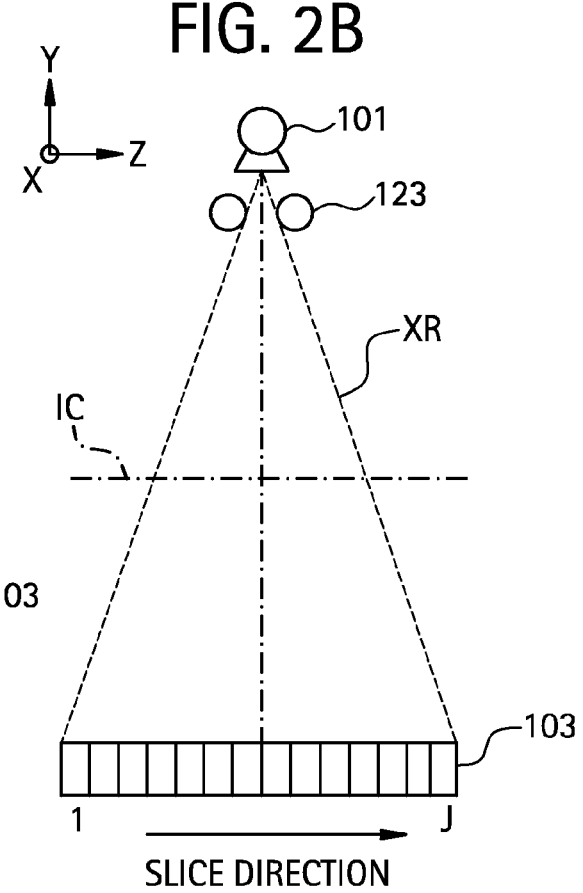

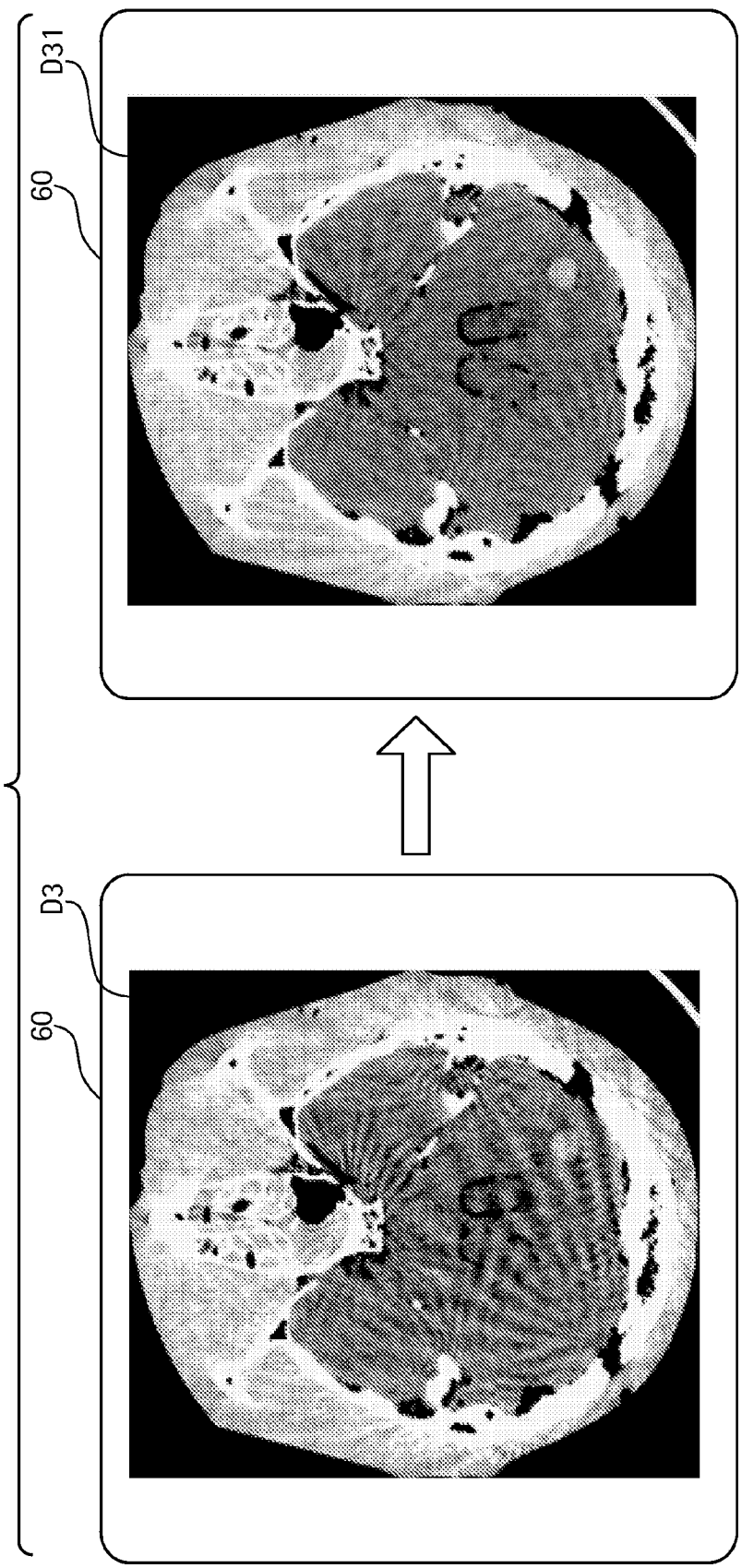

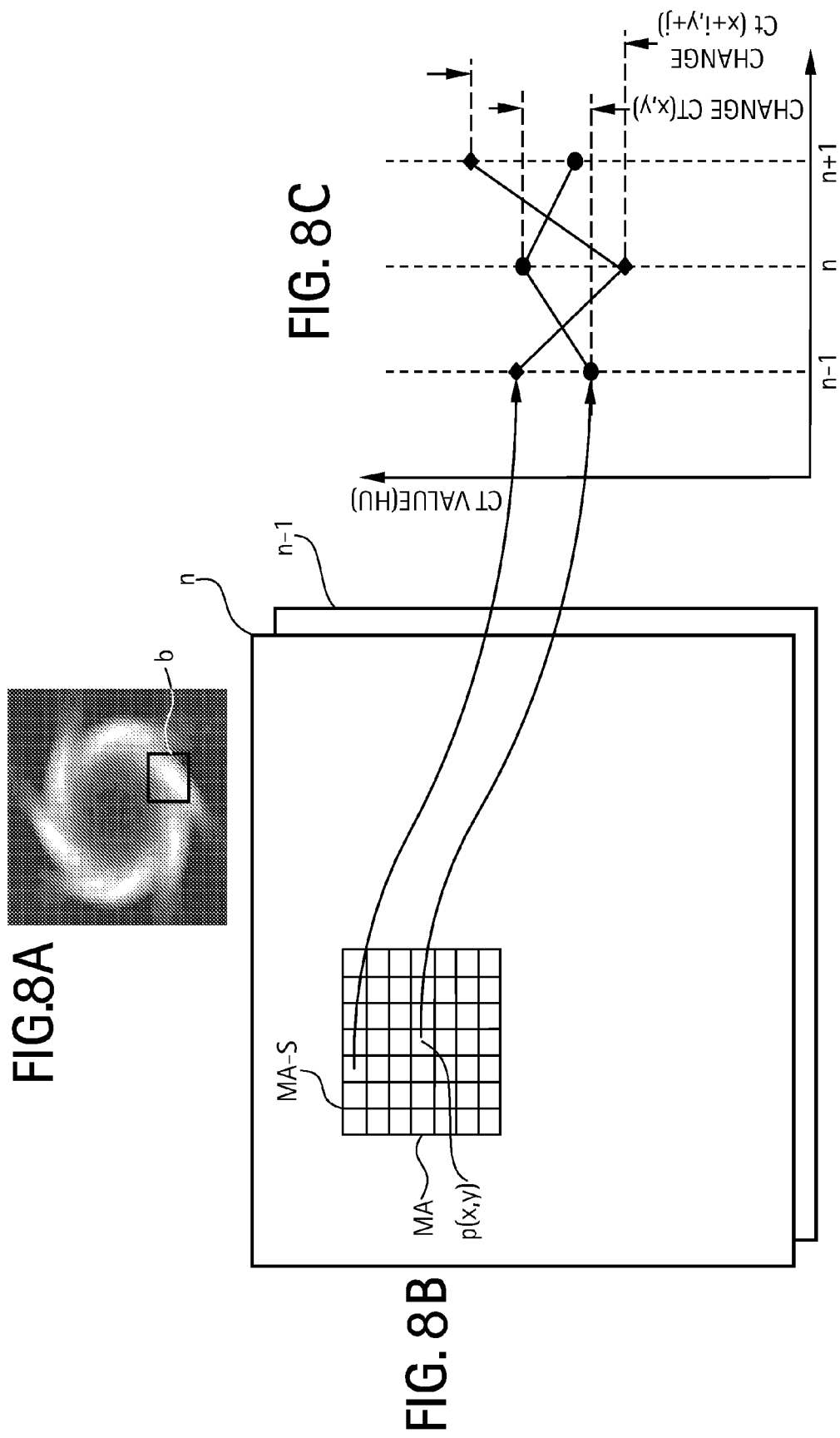

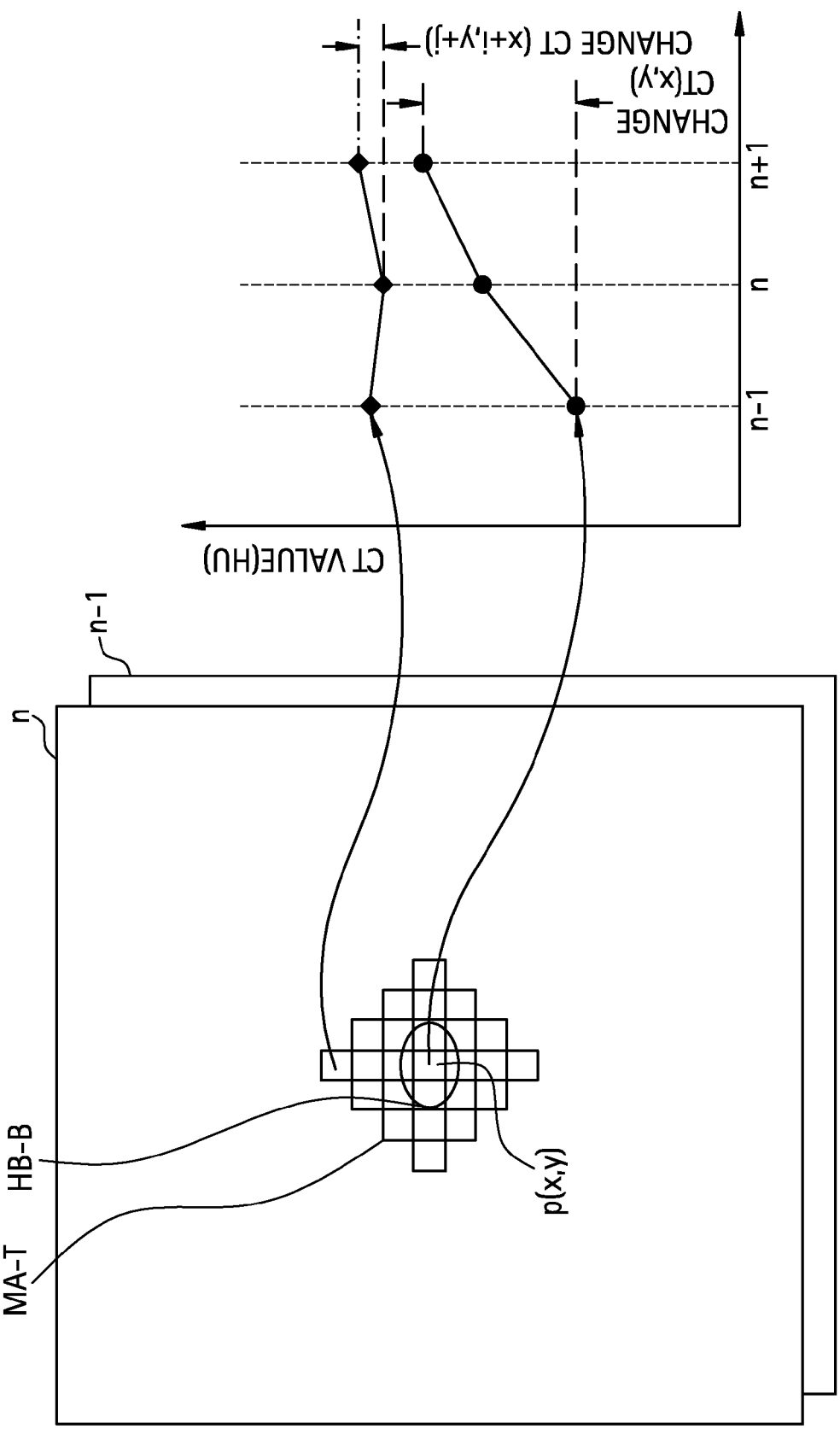

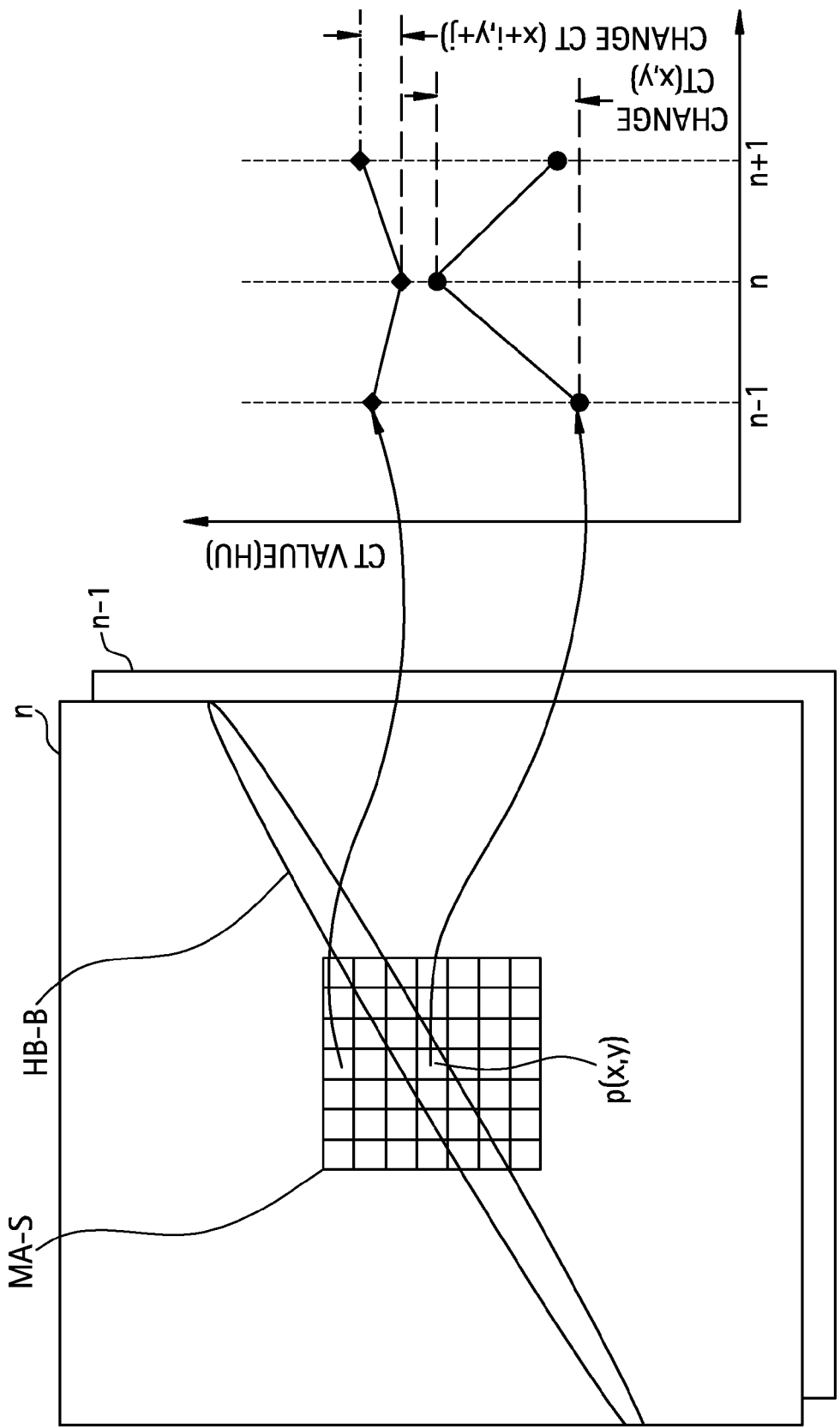

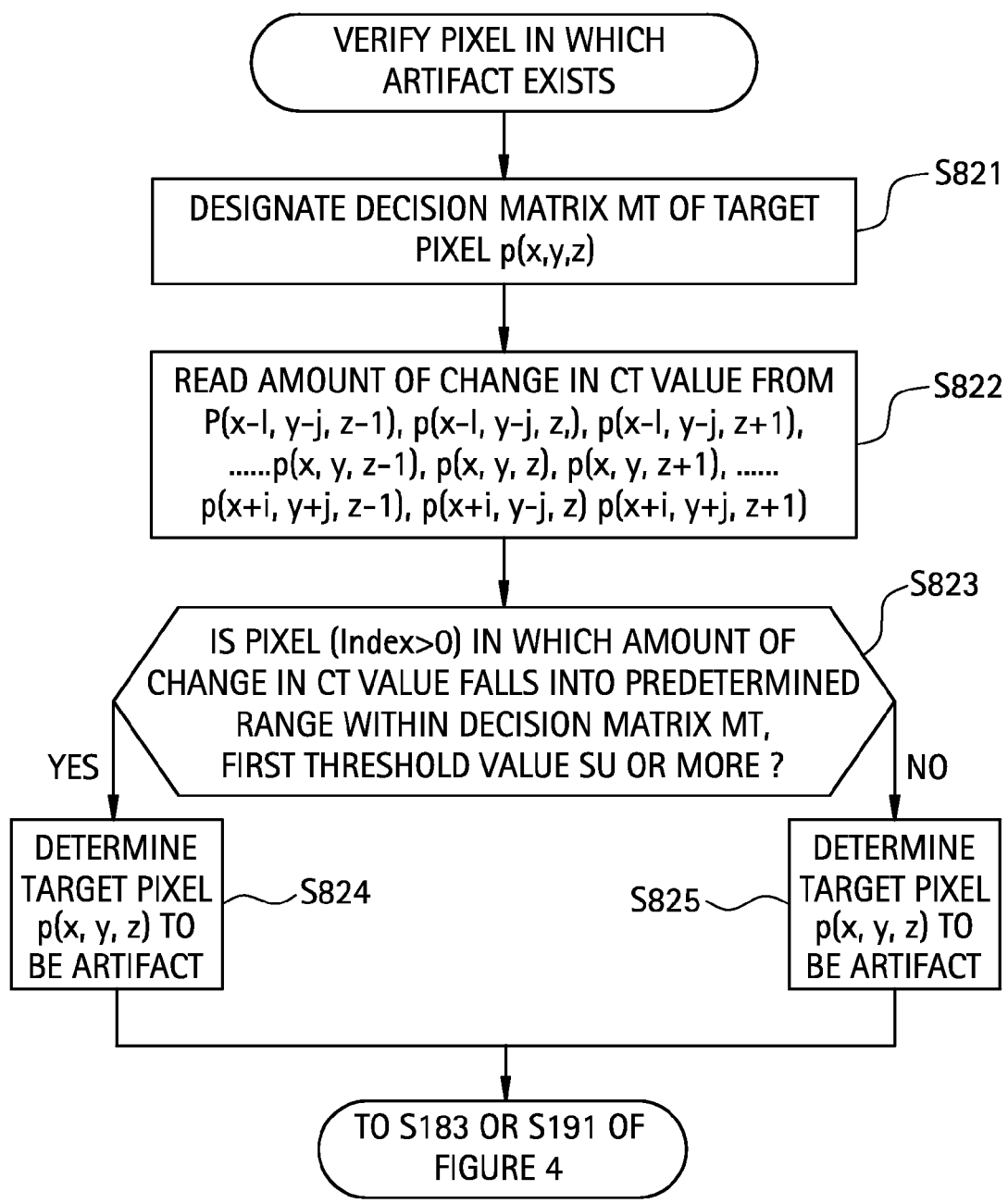

ARTIFACT RATIO=0.12

ARTIFACT RATIO=0.03

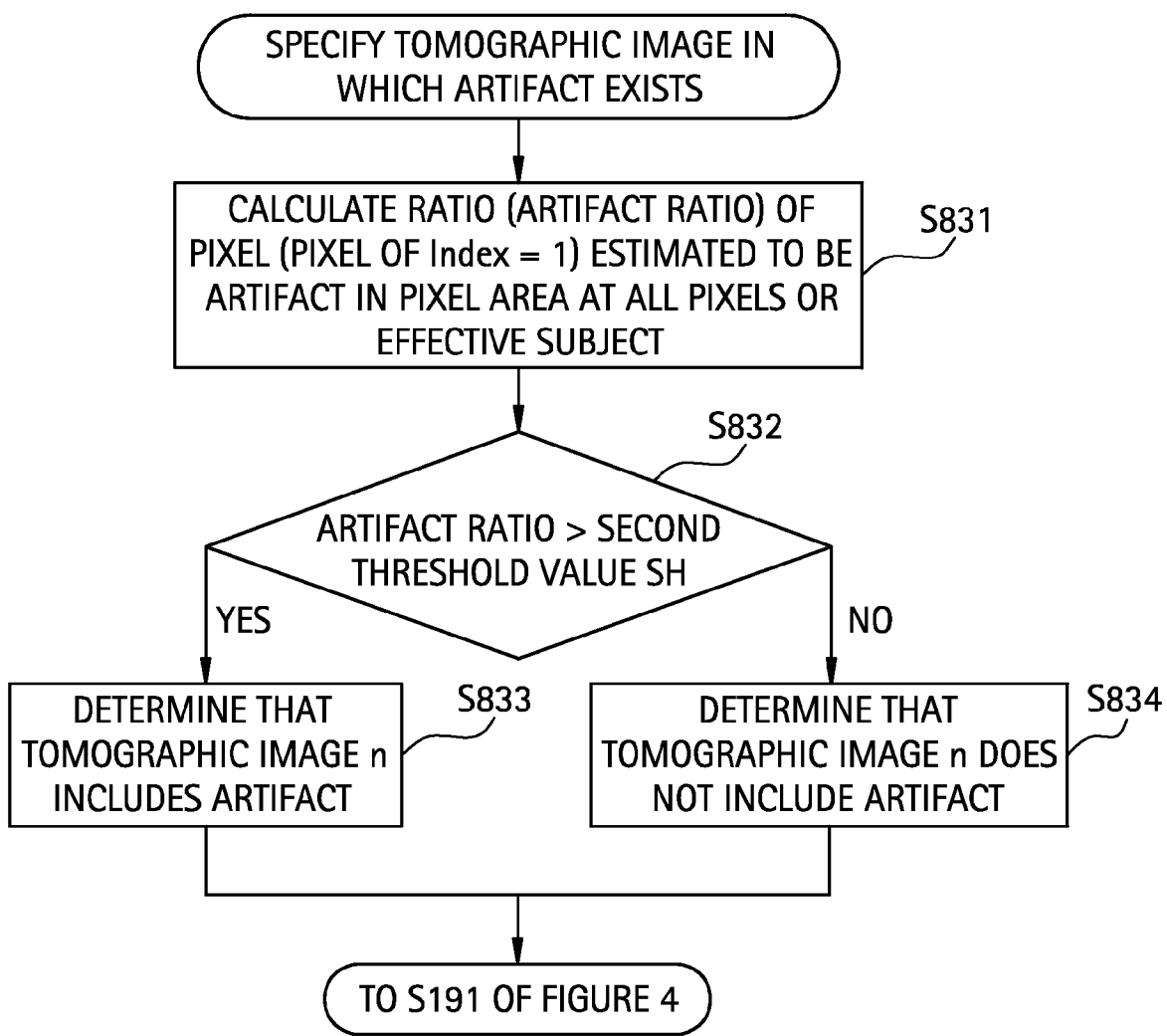

X-RAY TOMOGRAPHY APPARATUS AND ARTIFACT REDUCING METHOD

CROSS REFERENCE TO RELATED APPLICATIONS

This application claims the benefit of Japanese Patent Application No. 2006-292156 filed Oct. 27, 2006.

BACKGROUND OF THE INVENTION

The present invention relates to an X-ray tomography apparatus which displays tomographic images having less influence over artifacts such as a cone-beam artifact, a windmill artifact, etc., at an X-ray CT (Computed Tomography) apparatus or the like, and an artifact reducing method thereof.

In a multi-slice X-ray computer tomography (X-ray CT) apparatus, the number of slices is now increasing to 64 or 256. There have been known various cone-beam image reconstruction algorithms using a helical scan of the X-ray CT apparatus. However, one problem common among the cone-beam image reconstruction algorithms is that a sampling interval in a body-axis direction (called also z direction or slice direction) of a subject is insufficient. These algorithms run counter to Nyquist's theorem and cause vertical windmill-like artifacts within each reconstructed image due to high-frequency components. That is, when the resolution of a detector is insufficient for a structure and a helical pitch is made larger at the helical scan, interpolation calculations cannot be carried out ideally and hence the windmill-like artifacts occur on an image.

In order to reduce such windmill-like artifacts, multi-point interpolation is performed in the z direction to reduce the width of a fluctuation of a target signal, thereby casting the windmill-like artifacts into the shade. In Japanese Unexamined Patent Publication No. 2003-325502, for example, an interpolation process is performed in a z direction upon execution of a reconstruction function convolution process thereby to attempt to reduce windmill-like artifacts.

SUMMARY OF THE INVENTION

In the method for performing the multi-point interpolation in the z direction to reduce the artifacts, however, interpolation is effected even on image areas with no artifacts developed therein, thus leading to a reduction in resolution in a Z direction, whereby a distinct tomographic image cannot be obtained by a more increase in resolution.

Therefore, the present invention aims to provide an X-ray tomography apparatus that positively extracts artifacts without decreasing resolution in a Z direction thereby to reduce the artifacts, and an artifact reducing method thereof.

In the present invention, artifacts are reduced only with respect to image areas each having the artifact developed therein, from a three-dimensionally back-projected tomographic image. The three-dimensionally back-projected tomographic image is used as it is with respect to a region free of the occurrence of the artifacts and the tomographic image is displayed. Therefore, a distinct tomographic image can be obtained with respect to the image area free of the occurrence of the artifacts without reducing resolution in a z direction.

An X-ray tomography apparatus according to a first aspect comprises scan device for exposing X rays to a subject while at least one of a gantry and a table is being moved along a body-axis direction of the subject, thereby to create projection data of the subject, a first artifact determination unit for determining each of pixels contained in a tomographic image obtained by backprojecting the projection data as an artifact, a second artifact determination unit for, with the pixel determined to be the artifact by the first artifact determination unit as a target, setting a decision pixel area containing the target pixel and areas lying around the target pixel, and re-determining the target pixel as an artifact where each pixel judged to be the pixel at which the artifact is capable of being generated at the first artifact determination unit exists beyond a predetermined reference, and an artifact reduction unit for effecting an image process for reducing an artifact on each pixel finally judged to be an artifact.

In the X-ray tomography apparatus according to the first aspect, the first artifact determination unit first determines that an artifact exists in each of pixels contained in a tomographic image. Further, the second artifact determination unit re-determines that the pixel judged as the artifact by the first artifact determination unit is as an artifact where the pixel is beyond a predetermined reference or standard. Therefore, it is doubly determined whether each pixel in the tomographic image is as the artifact. Image processing can be effected only on the pixel in which the artifact judged in this way occurs, to reduce the artifact. Since pixels other than the artifacts are not subjected to interpolation processing, resolution in the body-axis direction is not degraded.

The X-ray tomography apparatus according to a second aspect further includes artifact ratio calculating device for calculating a ratio at which each pixel judged to be the artifact is occupied in the tomographic image, and a third artifact determination unit for re-determining the pixel as an artifact when the ratio is larger than a predetermined threshold value.

The X-ray tomography apparatus according to the second aspect calculates a ratio at which the target pixel re-determined to be the artifact is occupied in each tomographic image. That is, there is a tomographic image in which no artifacts appear depending upon the ratio. Therefore, even when artifacts are re-determined to exist in an image, it can also be determined that no artifacts occur in a tomographic image smaller than a predetermined ratio as the entire tomographic image. Thus, the target pixel specifies the pixel corresponding to the artifact, and image processing can be effected only on the specified pixel with the artifact developed therein to reduce the artifact.

In the X-ray tomography apparatus according to a third aspect, the first artifact determination unit determines artifacts according to the amount of change in CT value in the body-axis direction among a plurality of tomographic images obtained by backprojecting the projection data.

The amount of change in CT value in the body-axis direction is specified through experiments or the like. Whether the amount of change in CT value is contained in a predetermined range, is determined, thereby determining each pixel in which an artifact is being developed. In the constitution according to the third aspect, of the tomographic image, it is determined whether the amount of change in CT value is included in the predetermined range, thereby determining each pixel in which an artifact is being developed.

In the X-ray tomography apparatus according to a fourth aspect, the image process for reducing the artifacts at the artifact reduction unit is to multiply a plurality of pixels in the body-axis direction by weighting factors and add the results of multiplication, and reduce an artifact of each target pixel in the corresponding tomographic image.

In the constitution of the third aspect, the plurality of pixel areas in the body-axis direction are multiplied by their corresponding weighting factors and the results of multiplication are added together, and artifacts developed in a pixel area of each tomographic image are reduced.

In the X-ray tomography apparatus according to a fifth aspect, the artifact reduction unit changes the weighting factor according to the number of the plural pixel areas in the body-axis direction in the fourth aspect.

In the constitution of the third aspect, the weighting factor can be changed based on the number of the plural pixel areas in the body-axis direction, corresponding to, for example, 3 in the case of one slice image in the neighborhood of a target area, and 2n+1 in the case of n slice images in the neighborhood thereof.

In the X-ray tomography apparatus according to a sixth aspect, each of the decision pixel areas is shaped in the form of a quadrangle or a polygon.

In the constitution of the sixth aspect, the decision pixel area may be quadrangular or polygonal in shape according to a tomographic image display method or an imaging condition or the like.

In the X-ray tomography apparatus according to a seventh aspect, the number of the pixels constituting the decision pixel area is changed according to an enlarged display of each tomographic image and a reduced display thereof.

In the constitution of the seventh aspect, the size of an artifact on the screen or the size of a region thereon changes by the enlarged display of the tomographic image and its reduced display. Varying the size of the decision pixel area according to it makes it possible to specify each pixel corresponding to the artifact more accurately.

In the X-ray tomography apparatus according to an eighth aspect, the reference at the first artifact determination unit can be made variable.

Artifacts are different in the way of appearing according to the imaging condition or imaging region of the subject. If, for example, a region in which artifacts almost unappear is taken, then no problem occurs even though the first threshold value is relaxed to 90% to 85%. Thus, if the reference at the first artifact determination unit can be made variable in consideration of the artifacts that appear in the tomographic image and the resolution in the body-axis direction, then a tomographic mage that an operator aims can be obtained.

In the X-ray tomography apparatus according to the ninth aspect, the reference at the second artifact determination unit can be made variable.

In the ninth aspect, artifacts are different in the way of appearing according to the imaging condition or imaging region or the like of the subject. Each pixel corresponding to the artifact is stored and cast into the shade as much as possible. On the one hand, interpolation processing may preferably be not effected on each normal pixel. Therefore, if the reference at the second artifact determination unit can be made variable in consideration of the artifacts that appear in the tomographic image and the resolution in the body-axis direction, then a tomographic mage that an operator aims can be obtained.

According to the X-ray tomography apparatus and the artifact reducing method of the present invention, each pixel with an artifact developed therein can be reliably specified because the pixel with the artifact developed therein is verified. Artifacts are reduced only with respect to pixels each having the artifact developed therein, from a three-dimensionally back-projected tomographic image. A tomographic image in which the three-dimensionally back-projected tomographic image is used as it is with respect to a region free of the occurrence of the artifacts, can be displayed.

BRIEF DESCRIPTION OF THE DRAWINGS

FIG. 6 is an example in which a tomographic image D3 (x, y, z) prior to execution of an artifact reduction process and a tomographic image D31 (x, y, z) subjected to the artifact reduction process are displayed on a display 60.

FIG. 8(a) is a diagram showing a windmill artifact, FIG. 8(b) is an enlarged diagram of an area surrounded by a frame b of FIG. 8(a), and FIG. 8(c) is a graph showing the amount of change in CT value.

FIG. 9(a) is a diagram showing a vessel portion HB-B at which the direction in which a blood vessel extends changes suddenly, and FIG. 9(b) is a graph showing the amount of change in CT value.

FIG. 10(a) is a diagram showing a vessel portion HB-B extending to an XY plane, and FIG. 10(b) is a graph showing the amount of change in CT value.

FIG. 11 is a flowchart for verifying a target pixel in which artifacts exist.

FIG. 13 is a diagram showing a flowchart for performing an artifact reduction process after examinations of artifact ratios.

DETAILED DESCRIPTION OF THE INVENTION

Configuration of X-Ray Tomography Apparatus.

Figure 1:
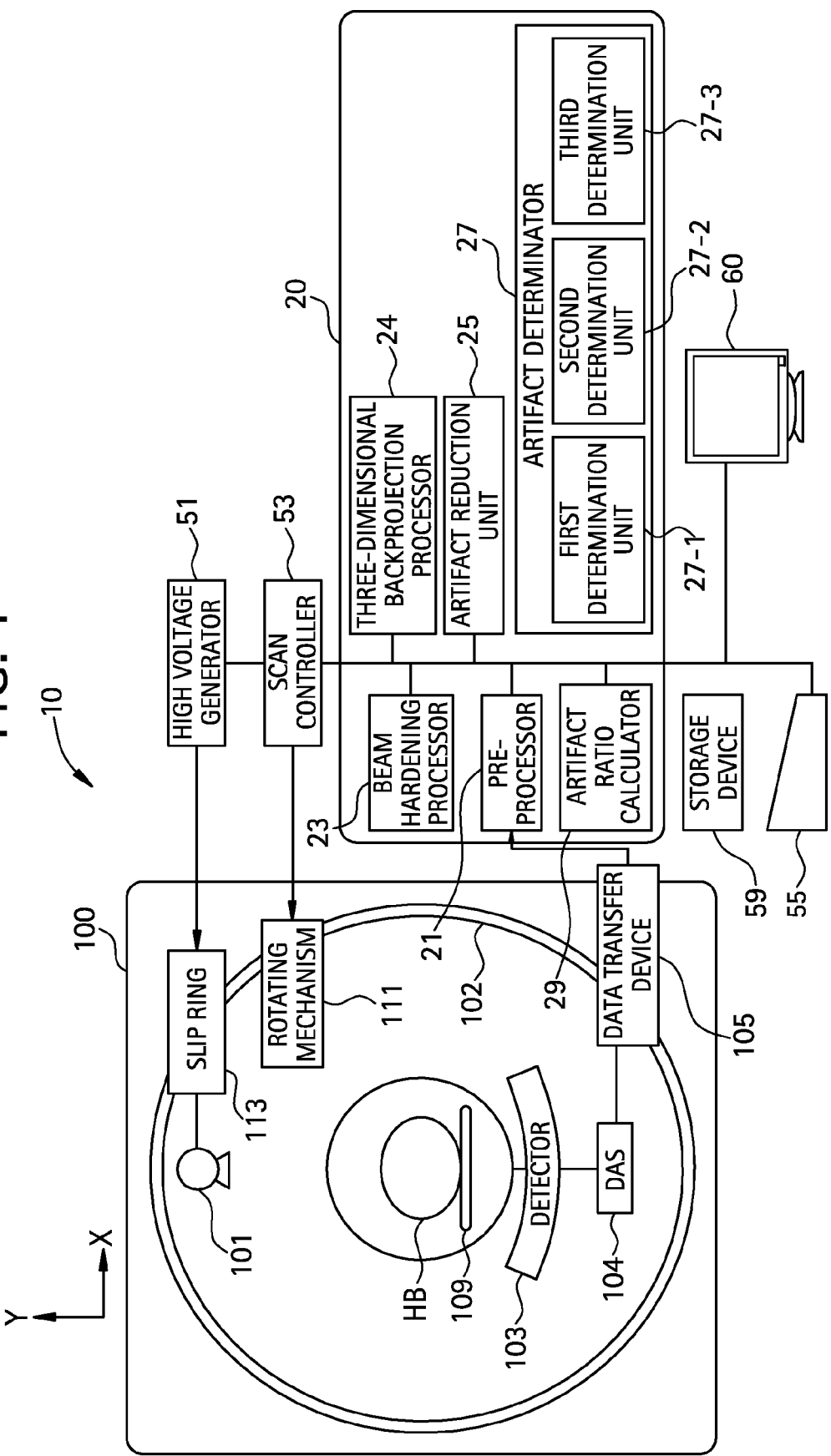
FIG. 1 is a block diagram showing a configuration of an X-ray CT apparatus 10 according to the present embodiment.

FIG. 1 is a block diagram showing a configuration of an X-ray computed tomography apparatus (X-ray CT apparatus) 10 according to the present embodiment. The X-ray tomography apparatus 10 is equipped with a gantry 100 and a table 109 for inserting a subject HB in an imaging area of the gantry 100. The table 109 is moved in a Z direction corresponding to the direction of a body axis of the subject HB. The gantry 100 has a rotating ring 102 and includes an X-ray tube 101 for exposing an X-ray beam XR shaped in the form of a cone beam to the rotating ring 102, and a multi-row X-ray detector 103 disposed opposite to the X-ray tube 101. The multi-row X-ray detector 103 detects X rays transmitted through the subject HB.

The multi-row X-ray detector 103 comprises scintillators and photodiodes. A data acquisition circuit 104 generally called DAS (data acquisition system) is connected to the multi-row X-ray detector 103. An I-V converter for converting a current signal for each channel of the multi-row X-ray detector 103 to a voltage, an integrator for periodically integrating the voltage signal in sync with an X-ray irradiation cycle or period, a preamplifier for amplifying a signal outputted from the integrator, and an analog-to-digital converter for converting a signal outputted from the preamplifier to a digital signal are provided for each channel in the data acquisition circuit 104. Digital signals sent from the data acquisition circuit 104 are transmitted to an image processor 20 through a data transfer device 105.

A high voltage generator 51 for supplying a voltage to the X rays is provided on the operation console side. The high voltage generator 51 periodically generates a high voltage and supplies the high voltage to the X-ray tube 101 through a slip ring 113.

A scan controller 53 on the operation console side executes a plurality of scan patterns such as an axial scan, a helical scan, a variable pitch helical scan. The axial scan is a scan method for rotating the X-ray tube 101 and the multi-row X-ray detector 103 each time the table 109 is moved by a predetermined pitch in the Z-axis direction thereby to obtain or acquire projection data. The helical scan is a scan method for moving the table 109 at a predetermined velocity in a state in which the X-ray tube 101 and the multi-row X-ray detector 103 are being rotated, thereby to acquire raw data. The variable pitch helical scan is a scan method for varying the velocity of the table 109 while the X-ray tube 101 and the multi-row X-ray detector 103 are being rotated by a rotating mechanism 111 in a manner similar to the helical scan thereby to acquire raw data. The scan controller 53 drives the rotating mechanism 111 in sync with the high voltage generator 51 and exercises control over scans such as periodic acquisition of raw data by the data acquisition circuit 104, etc.

An input device 55 comprises a keyboard or a mouse that receives an input from an operator. A storage device 59 stores programs, X-ray detector data, projection data and X-ray tomographic images therein. The image processor 20 effects a pre-process, an image reconstruction process, a post-process and the like on the projection data sent from the data acquisition circuit 104. A display 60 displays an operation screen and displays an image-reconstructed tomographic image.

Configuration of Image Processor.

The image processor 20 includes a pre-processor 21, a beam hardening processor 23, a three-dimensional backprojection processor 24, an artifact reduction unit 25, an artifact determinator 27 (first determination unit 27-1, second determination unit 27-2 and third determination unit 27-3), and an artifact ratio calculator 29.

The pre-processor 21 corrects channel-to-channel sensitivity ununiformity with respect to the raw data acquired by the data acquisition circuit 104 and executes a pre-process such as an X-ray dosage correction for correcting an extreme reduction in signal strength or a signal omission due to an X-ray strong absorber, principally, a metal portion. Incidentally, data done with the pre-process is called projection data in the present embodiment.

The beam hardening processor 23 effects correction processing on beam hardening of the projection data. The beam hardening is of a phenomenon that the absorption of X rays changes due to a transmission thickness even in the case of the same material and thereby a CT value (luminance) on each CT image varies. Particularly, it means that an energy distribution of radiation transmitted through a subject is biased to the high energy side. Therefore, the beam hardening is corrected in a slice direction of the projection data and a channel direction thereof.

The three-dimensional backprojection processor 24 receives the projection data pre-processed by the pre-processor 21 and reconstructs images, based on the projection data. The projection data is subjected to fast-Fourier transform (FFT) for transforming it to a frequency domain and convoluted with a reconstruction function Kernel (j), followed by being subjected to inverse Fourier transform. The three-dimensional backprojection processor 24 effects a three-dimensional backprojection process on the projection data subjected to the convolution processing of the reconstruction function Kernel (j) to determine a tomographic image (xy plane) for each body-axis direction (Z direction) of the subject HB. The three-dimensional backprojection processor 24 allows the storage device 59 to store the tomographic image.

The artifact reduction unit 25 reads the tomographic image subsequent to the three-dimensional backprojection from the storage device 59 and performs an artifact reduction process thereon. The artifact reduction unit 25 allows the storage device 59 to store the tomographic image reduced in artifact and causes the display 60 to display it.

The artifact determinator 27 has the first determination unit 27-1, the second determination unit 27-2 and the third determination unit 27-3. The first determination unit 27-1 estimates the occurrence of artifacts from the amount of change in CT value in pixels of each tomographic image. The second determination unit 27-2 re-determines the corresponding pixel estimated to have developed the artifacts, using a decision matrix including the pixel. Further, the third determination unit 27-3 determines at what ratio the artifacts are occupied in each tomographic image or the subject HB lying in the tomographic image, and verifies the presence of the artifacts. Since image resolution in the body-axis direction is degraded with the execution of the artifact reduction process, the artifact reduction process may not be performed if the artifact is a negligible weak artifact. Therefore, the artifact determinator 27 has the plurality of determination units. These determination units have a plurality of criteria of judgment according to imaging conditions or circumstances and the like.

The artifact ratio calculator 29 calculates how the pixel with the artifact developed therein makes up the proportion in the tomographic image or the subject HB in the tomographic image.

Figures 2, 12A:
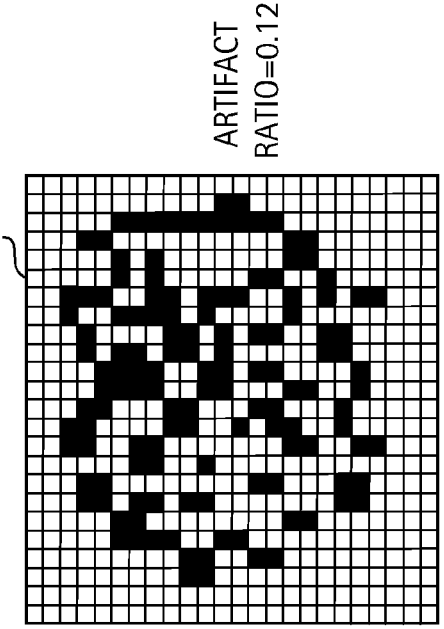
FIGS. 2(a) and 2(b) are diagrams showing geometrical layouts illustrative of an X-ray tube 10 and a multi-row X-ray detector 103.
FIGS. 12(A1), 12(A2), (12B1), and 12(B2) are diagrams showing tomographic images prior to being subjected to an artifact reduction process, of the head of a subject, and reconstruction areas P.
Figures 2, 12B:
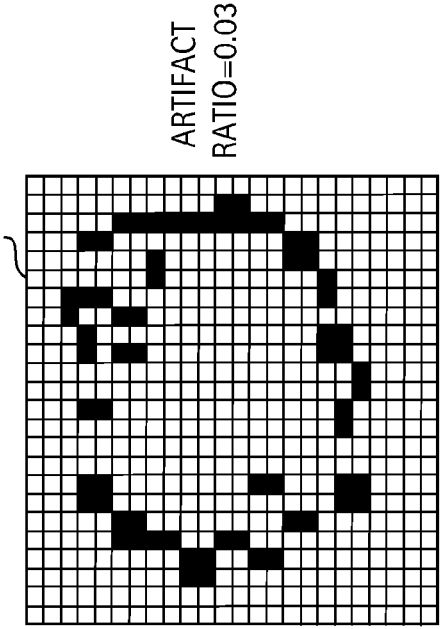
Figures 1, 12A:
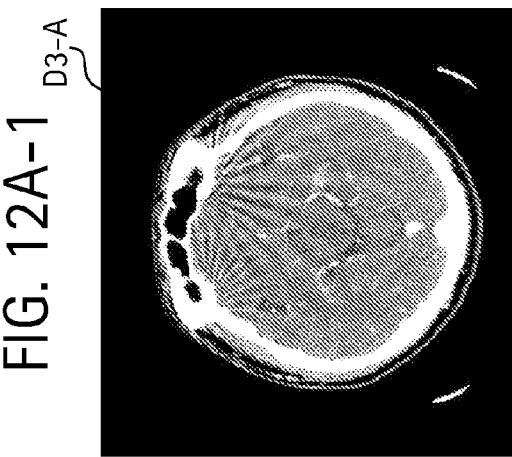
Figures 1, 12B:

FIGS. 2(a) and 2(b) are diagrams showing geometrical layouts of the X-ray tube 101 and the multi-row X-ray detector 103. FIG. 2(a) is a diagram showing the geometrical layouts of the X-ray tube 101 and the multi-row X-ray detector 103 as viewed from an xy plane, and FIG. 2(b) is a diagram showing the geometrical layouts of the X-ray tube 101 and the multi-row X-ray detector 103 as viewed from a yz plane. An anode of the X-ray tube 101 generates an X-ray beam XR called a cone beam. When the direction of a central axis of the cone beam is parallel to a y direction, it is assumed to be a view angle 0°. The multi-row X-ray detector 103 has X-ray detector rows corresponding to J rows in the z-axis direction (slice direction), for example, 256 rows. Each of the X-ray detector rows has X-ray detector channels corresponding to I channels as viewed in the channel direction, e.g., 1024 channels. In FIG. 2(a), more X rays in the X-ray beam XR emitted from the X-ray focal point of the X-ray tube 101 are applied in the center of an image reconstruction area P by a beam forming X-ray filter 121, whereas lesser X rays in the X-ray beam XR are applied at portions around the image reconstruction area P. Thus, the X rays are absorbed into the subject HB existing inside the image reconstruction area P after spatial control on the X-ray dosage, and the transmitted X rays are acquired by the multi-row X-ray detector 103 as raw data.

In FIG. 2(b), the X-ray beam XR emitted from the anode of the X-ray tube 101 is controlled in the direction of slice thickness of a tomographic image by an X-ray collimator 123 and hence the X rays are absorbed into a subject HB existing in the vicinity of the central axis IC of rotation, and the penetrated X rays are acquired by the multi-row X-ray detector 103 as raw data. Each of the raw data acquired by the multi-row X-ray detector 103 after the X rays have been applied to the subject HB, is A/D-converted by the data acquisition circuit 104 as viewed from the multi-row X-ray detector 103, followed by being inputted to the image processor 20 via the data transfer device 105. The raw data inputted to the image processor 20 is processed by the image processor 20 in accordance with the corresponding program of the storage device 59 and image-reconstructed into a tomographic image, which is followed by being displayed on the display 60. Incidentally, although the multi-row X-ray detector 103 has been applied in the present embodiment, a two-dimensional X-ray area detector of a matrix structure typified by a flat panel X-ray detector can also be applied.

Operation Flowchart for Tomogram Photography.

Figure 3:
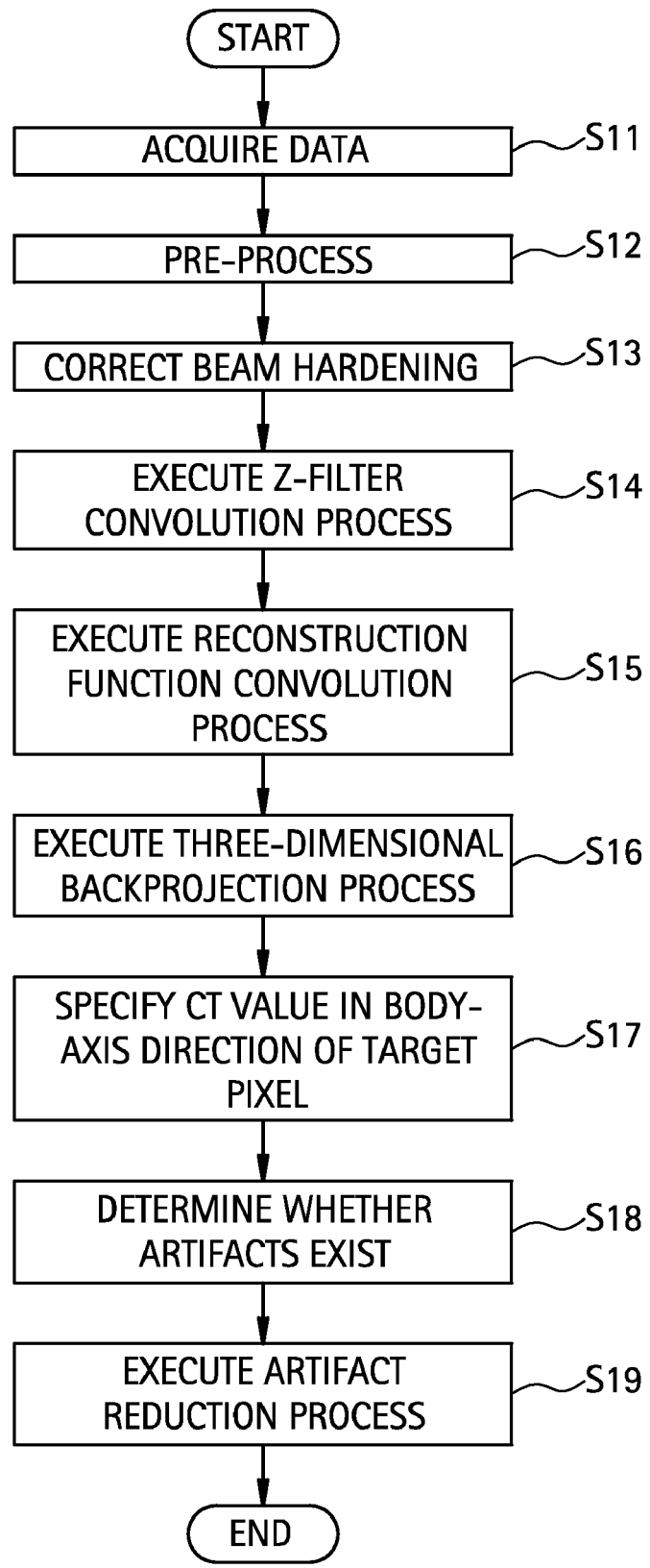
FIG. 3 is a flowchart schematically showing a tomographic image photographing operation of the X-ray CT apparatus 10 of the present invention.

FIG. 3 is a flowchart showing the outline of a tomographic image photographing operation of the X-ray CT apparatus 10 of the present invention.

At Step S11, a helical scan is executed to rotate the X-ray tube 101 and the multi-row X-ray detector 103 about the subject HB and acquire data from the multi-row X-ray detector 103 while the table 109 is being linearly moved. A z-direction position Ztable (view) is added to raw data D (view, j, i) (where j=1 to ROW and i=1 to CH) expressed in a view angle view, a detector row number j and a channel number i, and the acquisition of data in a constant-velocity range is performed.

At Step S12, the raw data D0 (view, j, i) is subjected to a pre-process and converted to projection data. An offset correction, a logarithmic translation, an X-ray dosage correction and a sensitivity correction are performed.

At Step S13, a beam hardening correction is effected on the pre-processed projection data D01 (view, j, i) and converted to projection data D1 subjected to the beam hardening correction. The beam hardening correction at Step S13 can be performed by a multiplication computation of a polynomial, for example. Since, at this time, the independent beam hardening corrections can be performed every j row as viewed in the slice direction of the multi-row X-ray detector 103, it is possible to correct the difference in X-ray energy characteristic between the detectors placed every row if X-ray tube voltages are different according to imaging conditions.

At Step S14, a z-filter convolution process for exposing filters in the slice direction (z direction) is effected on the projection data D1 subjected to the beam hardening correction, and the projection data D1 is converted into projection data D11 subjected to the filter convolution process. That is, the z-filter convolution process is effected on projection data of the multi-row X-ray detector 103 at each view angle and each data acquisition system. When row-direction filter coefficients are changed for every channel, slice thicknesses can be controlled depending upon the distance from an image reconstruction center.

At Step S15, a reconstruction function Kernel (j) is convolution-processed with respect to the projection data D11 subjected to the filter convolution process. That is, the fast Fourier transform (FFT) for transforming the projection data D11 subjected to the filter convolution process into a frequency domain is preformed, and the reconstruction function Kernel (j) is convolution-processed for the projection data D11. Then, the inverse Fourier transform is performed to transform it into projection data D2 (view, j, i) subjected to a reconstruction function convolution process. Since the convolution process for the reconstruction function Kernel (j) and the reconstruction functions independent of one another every j row of the multi-row X-ray detector 103 can be carried out, the differences between noise characteristics and between resolution characteristics every row can be corrected.

At Step S16, a three-dimensional backprojection process is effected on the projection data D2 (view, j, i) subjected to the reconstruction function convolution process to determine backprojection data D3 (x, y, z). An image to be image-reconstructed is three-dimensionally image-reconstructed on a plane, i.e., an xy plane orthogonal to the z axis. The following reconstruction area P is assumed to be parallel to the xy plane.

At Step S17, the artifact reduction unit 25 detects each pixel with an artifact developed therein from the backprojection data D3 (x, y, z), based on the amount of change in CT value in the body-axis direction (z direction) of the CT value. As will be described later, the pixel with the artifact developed therein is contained within the amount of change in CT value in a predetermined range. Therefore, the artifact is estimated to exist if the amount of change in CT value in the predetermined range is taken.

At Step S18, the artifact determinator 27 and the artifact ratio calculator 29 perform a determining process on each pixel in which the artifact has been estimated to exist therein, to further ensure its estimation.

At Step S19, the artifact reduction unit 25 effects a filter process only on the detected image area with the artifacts developed therein. As to an image area with no artifacts developed therein, the backprojection data D3 (x, y, z) is used as a tomographic image D31 (x, y, z) as it is. Therefore, the resolution in the body-axis direction is maintained, so that a more distinct tomographic image can be obtained.

Operation Flowchart for Artifact Processing.

FIG. 4 is a flowchart used for performing a reduction in artifacts after determination of the backprojection data D3 (x, y, z) and is a flowchart showing, in detail, Steps S17 to S19 of the flowchart shown in FIG. 3. FIG. 5 is a conceptual diagram showing pixels of tomographic images based on the backprojection data D3 (x, y, z). Incidentally, a windmill artifact or a cone-beam artifact can be reduced by the present flowchart.

Figure 4A:
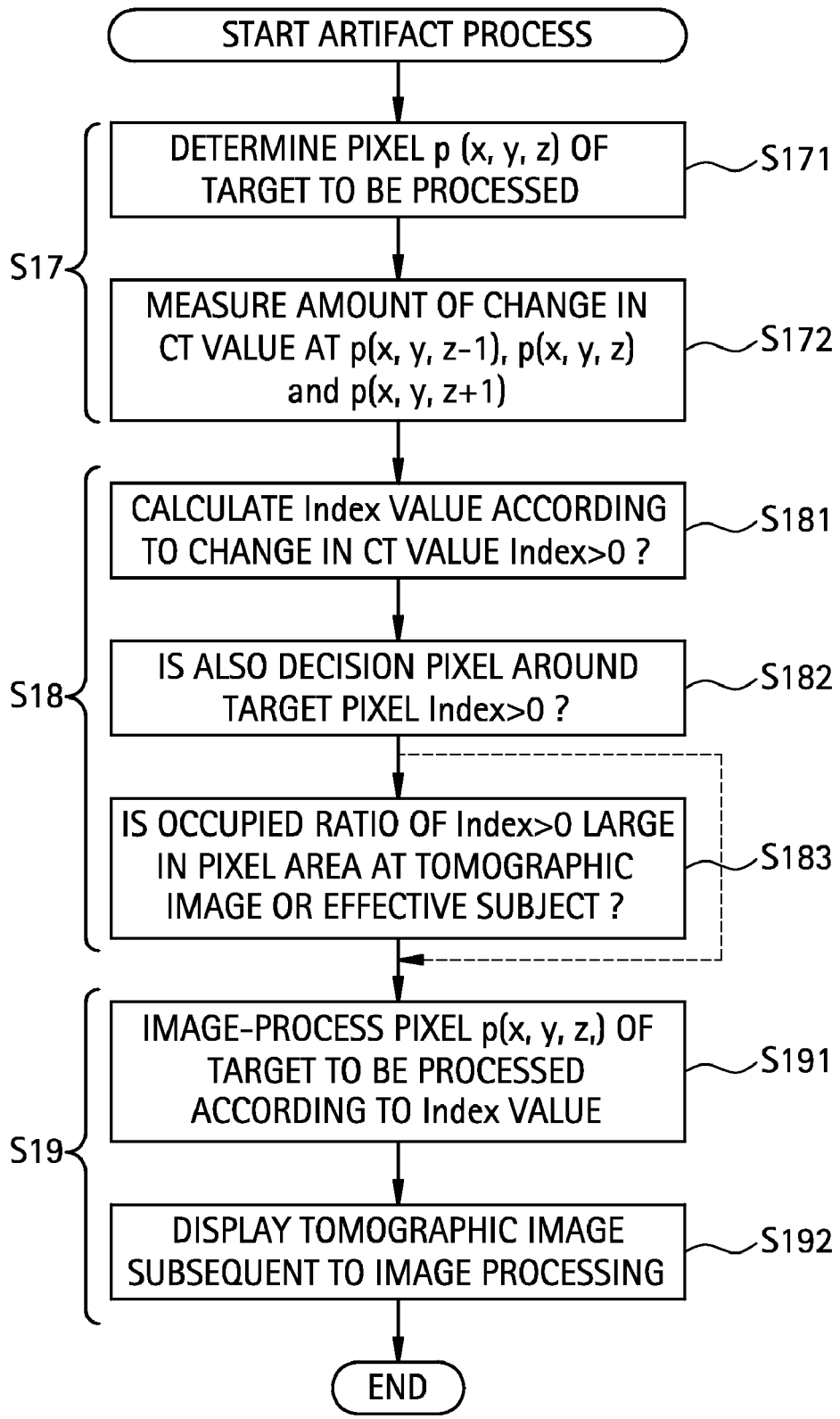
FIGS. 4(a) and 4(b) are flowcharts for reducing artifacts after determination of backprojection data D3.
Figure 5B:
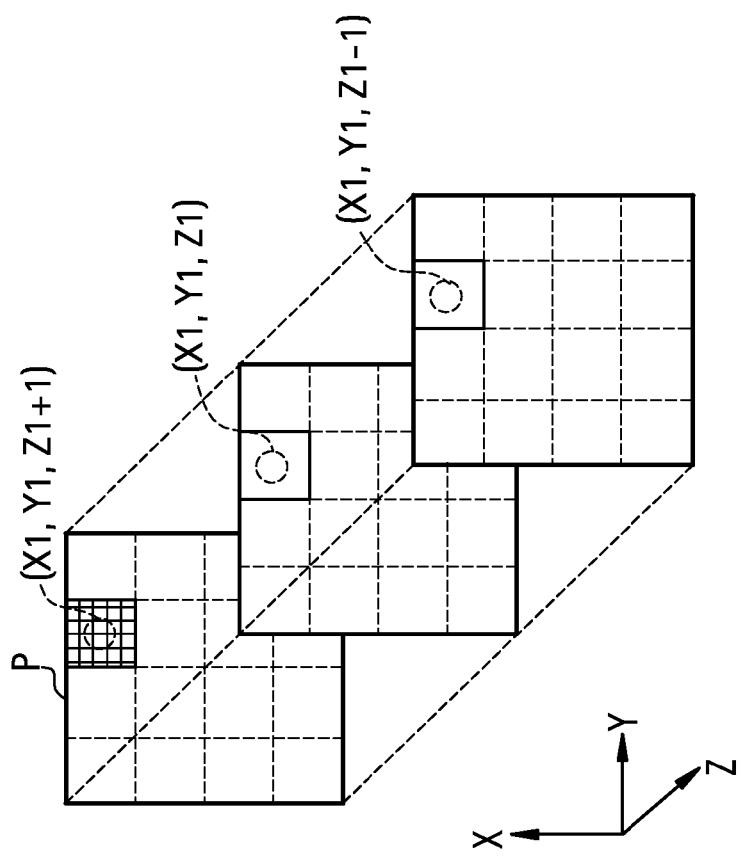
FIGS. 5(a) and 5(b) are conceptual diagrams showing pixels of tomographic images based on backprojection data D3 (x, y, z) and pixel areas thereof.
Figure 5A:
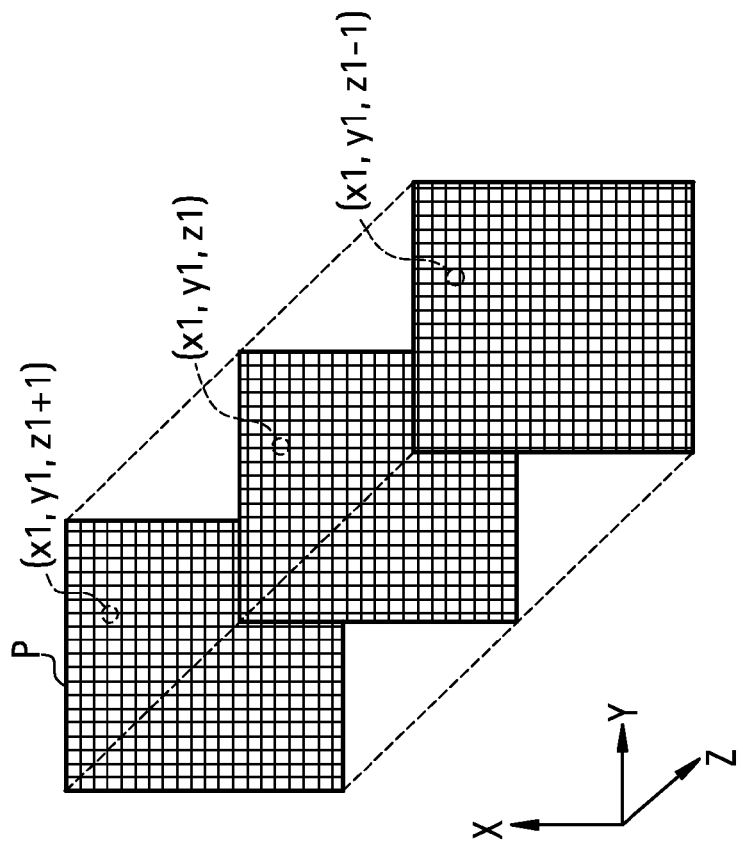

In FIG. 4(a), the z position of a subject HB that an operator wants to confirm is specified at Step S171. The artifact reduction unit 25 determines each pixel p (x, y, z) to be processed. If, for example, a square area of 512×512 pixels, which is parallel to the xy plane, is assumed to be a reconstruction area P as shown in FIG. 5(a), then x has a range from 1 to 512, and y also has a range from 1 to 512.

At Step S172, the artifact reduction unit 25 measures a change in CT value as viewed in the z direction for each pixel p (x, y, z) to be processed. Assume that, for example, changes in CT value in the z direction in the neighborhood of a pixel p (x1, y1, z1) to be processed in the reconstruction area P are as follows.

$p(x1,y1,z-1)=10$ HU (Hounsfield unit)

$p(x1,y1,z)=30$ HU $p(x1,y1,z+1)=50$ HU

It is understood from this that the amount of change of 40 HU exists from the difference between the minimum CT value and the maximum CT value in the neighborhood of the p (x1, y1, z) as viewed in the body-axis direction.

Here, FIG. 5(a) shows z-direction pixels in the neighborhood of the pixel p (x1, y1, z1). The change in VT value will be explained below based on the premise of a change for each pixel. However, an average CT value in a pixel area (X1, Y1, Z1) in which a plurality of pixels around one specific pixel are combined together, may be adopted, or the highest CT value or lowest CT value may be used. A pixel area constituted of a plurality of pixels is moved with being shifted for each specific pixel. Although the amount of change in CT value of one slice in the neighborhood of the pixel p (x1, y1, z1) to be processed has been measured as above, the amounts of change in CT values of n slices in the neighborhood thereof may be measured.

Next, at Step S181, the artifact determinator 27 (first determination unit 27-1) determines an index. This index can be determined by the following function. In the following equation, changes in the CT values of the n slices in the neighborhood of the pixel p (x, y, z) to be processed are measured and the intended index is determined from the changes.

index=f(p(x,y,z−n),p(x,y,z−n+1) . . . p(x,y,z) . . . p(x,y,z+n))

It means that the index is set so as to reduce artifacts with respect to pixels in which the artifacts are being developed, whereas the index is set so as to take advantage of the pixel p (x, y, z) to be processed, as it is with respect to pixels with no artifacts developed therein. Functions for determining the indexes will be explained using FIG. 7.

Assume that when the change in the CT value is given as p (x1, y1, z−1)=10 HU, p(x1, y1, z)=30 HU and p(x1, y1, z+1)=50 HU as the previous example, index=1 is reached.

At Step S182, the artifact determinator 27 (second determination unit 27-2) performs a determining process on each pixel in which the artifact has been estimated to exist therein, to further ensure its estimation. The artifact determinator 27 determines whether the pixels (index>0) in which the artifacts exist are large in number even at a plurality of pixel areas around the target pixel. This is because the occurrence of artifacts in only one target pixel is low. The present second determination unit 27-2 will be explained later in FIGS. 8 through 11.

At Step S183, the artifact ratio calculator 29 calculates at what ratio the pixels (index>0) in which the artifacts have been estimated to exist are occupied in all of 512×512 pixels where each tomographic image is expressed in a square of 512×512 pixels. This is because there is a possibility that if the ratio is extremely low, artifacts will not exist in its tomographic image. The artifact determinator 27 (third determination unit 27-3) determines, based on the ratio calculated by the artifact ratio calculator 29, whether the artifacts are being developed. The details thereof will be described later with reference to FIGS. 12 through 14. Incidentally, Step S183 need not necessarily be performed. This is because each pixel in which the artifact exists can substantially be grasped at Step S182. Therefore, the artifact processing may skip over Step S183 to proceed to Step S191 after the completion of Step S182 as indicated by a dotted line.

Next, at Step S191, the artifact reduction unit 25 image-processes the pixel p (x, y, z) to be processed, based on the index value to determine a pixel p' (x, y, z) subsequent to its processing. For example, the pixel p' is expressed in the following equation 1:

[Equation 1]

$$p'(x, y, z) = \sum_{i=start\_z}^{end\_z} p(x, y, z + i) * g(i, \text{index}) \quad (1)$$

where g (i, index) is a weighting factor of an ith slice in the z direction, based on the index. For example, weighting factors are set as follows every slice in the neighborhood of the pixel p (x1, y1, z1) to be processed.

Assume that when index=1, the weighting factor g applied or assigned to p (x1, y1, z−1) is g=0.33, the weighting factor g assigned to p (x1, y1, z) is g=0.33, and the weighting factor g assigned to p (x1, y1, z+1) is g=0.33. That is, each of pixels in which the artifacts are being developed is corrected to a pixel in which slices images in the neighborhood thereof are averaged. If n slice images are taken, then a value of g=1/(2n+1) may be used.

Assume that when index=0.5, the weighting factor g assigned to p (x1, y1, z−1) is g=0.2, the weighting factor g assigned to p (x1, y1, z) is g=0.6, and the weighting factor g assigned to p (x1, y1, z+1) is g=0.2. The influence of the pixel p (x, y, z) to be processed strongly remains in each pixel in which a weak artifact occurs, but slice images in the neighborhood of its pixel are also slightly added thereto.

Assume that when index=0, the weighting factor g assigned to p (x1, y1, z−1) is g=0, the weighting factor g assigned to p (x1, y1, z) is g=1, and the weighting factor g assigned to p (x1, y1, z+1) is g=0. The pixel p (x, y, z) to be processed is set to each pixel with no artifact so as to be used as it is.

Incidentally, the weighting factors g (i, index) may be stored in a lookup table or the like or stored as predetermined functions, based on information obtained from experiments or the like.

At Step S192, a tomographic image D31 (x, y, z) is obtained based on the p' (x, y, z) subsequent to the artifact reducing or reduction process. Then, it is displayed on the display 60.

FIG. 6 is an example in which a tomographic image D3 (x, y, z) prior to execution of the artifact reduction process of the present embodiment and a tomographic image D31 (x, y, z) subjected to the artifact reduction process are displayed on the display 60. The windmill artifact and the cone-beam artifact are strongly displayed on the tomographic image D3 (x, y, z). However, the influences of the windmill artifact and the cone-beam artifact are reduced as in the case of the tomographic image D31 (x, y, z) shown in the right drawing. In the tomographic image D 31 (x, y, z) shown in the right drawing, a pixel area with no artifacts becomes the same image as the tomographic image D3 (x, y, z) shown in the left drawing and remains same in resolution.

Figure 4B:
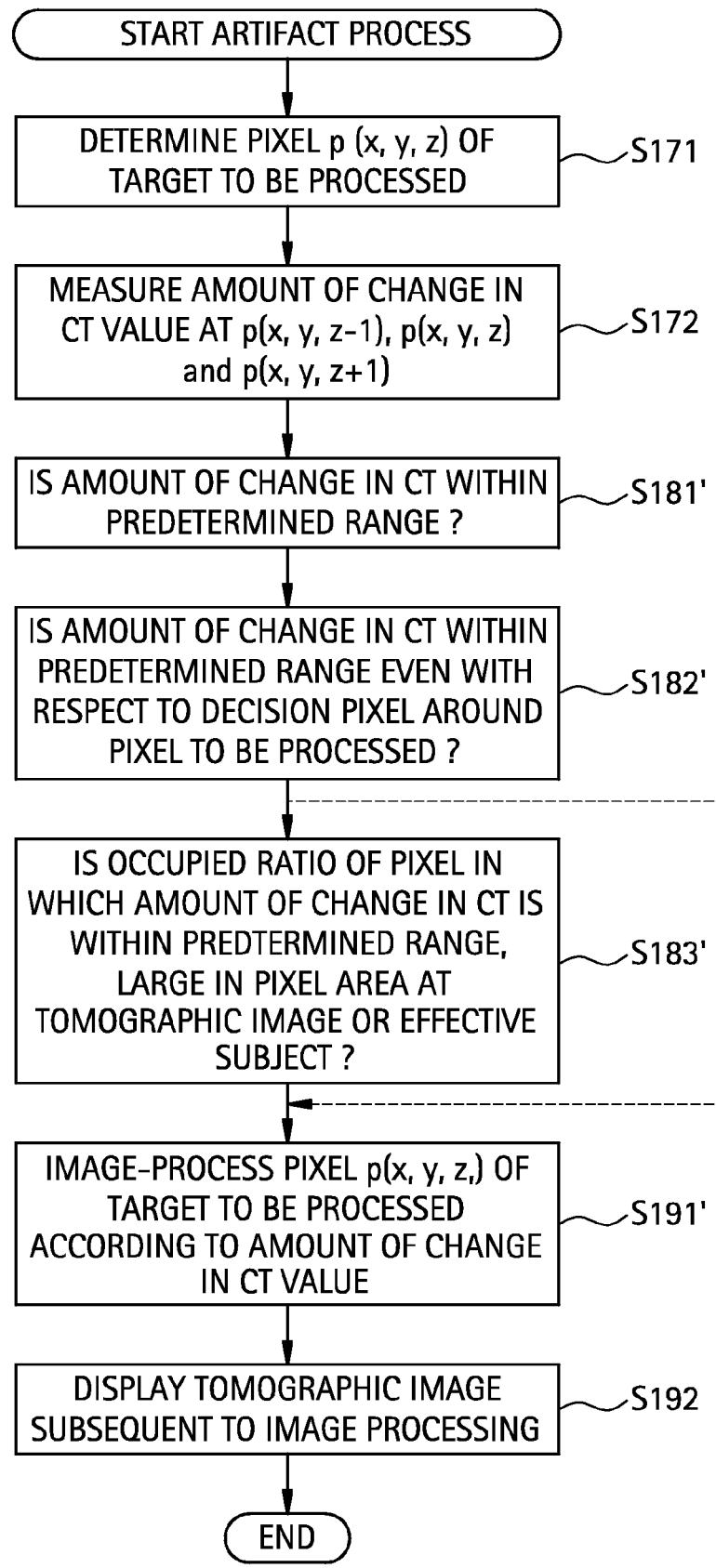

The flowchart shown in FIG. 4(b) is a flowchart using no index or index function (refer to FIG. 7) described at Step S181 of FIG. 4(a).

In the flowchart shown in FIG. 4(b), after the amount of change in CT value as viewed in the z direction has been measured for each pixel p (x, y, z) to be processed, at Step S172, it is determined at Step 181' whether the amount of change in CT value falls within a predetermined range. The predetermined range is from 3 HU to 300 HU, for example. It is next determined at Step S182' whether the amount of change in CT value falls within the predetermined range even at a plurality of pixel areas around the target pixel. When each tomographic image is expressed in the form of a square of 512×512 pixels, what is the ratio or proportion of pixels in which the amount of change in CT value falls within a predetermined range, of all the pixels, is calculated even at Step S183'. A weighting factor gv is also determined based on the amount of change in CT value at Step S191' without determining the index in the next place.

At Step S191', the pixel p (x, y, z) to be processed is image-processed based on the index value to determine a pixel p' (x, y, z) subsequent to its processing. The pixel p' (x, y, z) is expressed in the following equation 2, for example:

[Equation 2]

$$p'(x, y, z) = \sum_{i=start\_z}^{end\_z} p(x, y, z+i) * gv(i, CTv) \quad (2)$$

where gv (i, CTv) is a weighting factor of an ith slice in the z direction, based on the amount of change in CT value. For example, weighting factors are set as follows every slice in the neighborhood of the pixel p (x1, y1, z1) to be processed.

Assume that when the amount of change in CT value is 40 HU, the weighting factor gv applied or assigned to p (x1, y1, z−1) is gv=0.33, the weighting factor gv assigned to p (x1, y1, z) is gv=0.33, and the weighting factor gv assigned to p (x1, y1, z+1) is gv=0.33.

Assume that when the amount of change in CT value is 120 HU, the weighting factor gv assigned to p (x1, y1, z−1) is gv=0.2, the weighting factor gv assigned to p (x1, y1, z) is gv=0.6, and the weighting factor gv assigned to p (x1, y1, z+1) is gv=0.2.

Assume that when the amount of change in CT value is 200 HU, the weighting factor gv assigned to p (x1, y1, z−1) is gv=0, the weighting factor gv assigned to p (x1, y1, z) is gv=1.0, and the weighting factor g assigned to p (x1, y1, z+1) is gv=0.

Thus, the weighting factor gv may be determined directly from the amount of change in CT value. A method of directly determining the weighting factor gv needs to determine a large number of weighting factors gv every amount of change in CT value. Therefore, the quantities to be stored in the lookup table or the like depending upon the amount of change in CT value increase and the setting of the weighting factor gv becomes complex.

Example of Index Function.

FIG. 7 is an example illustrative of index functions for determining the indexes each used at Step S181 or Step S191 of FIG. 4(a).

Figure 7A:
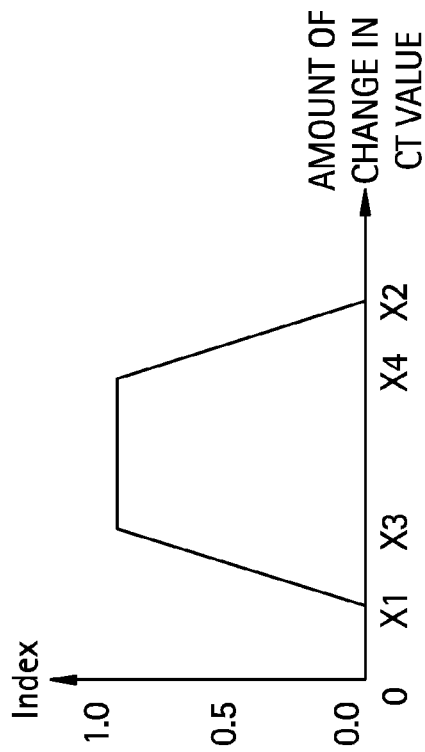
FIGS. 7(a), 7(b), 7(c), and 7(d) are diagrams showing index functions.

The index function of FIG. 7(a) is a function in which if the amount of change in CT value ranges from X1 to X3, then the index linearly changes from 0 to 1, and if the amount of change in CT value ranges from X3 to X2, then the index linearly changes from 1 to 0. Assume that, for example, X1 is 10 HU, X3 is 90 HU and X2 is 170 HU. When p (x1, y1, z−1)=10 HU, p (x1, y1, z)=30 HU and p (x1, y1, z+1)=50 HU with respect to a given image to be processed, the amount of change in CT value is 40 HU. In such a case, index=0.5 is determined in the index function shown in FIG. 7(a).

X1, X2 and X3 are set from 3 HU to 300 HU to 10 UH to 200 HU depending upon an imaging condition. When they are 200 HU or more, it means a portion or region that has changed from a soft tissue to the bone or vice versa. If they are 10 HU or less, it then means that the soft tissue is continuous in plural slice directions or the bone is continuous in the plural slice directions. On the other hand, it is estimated from the change in CT value from 3 HU to 300 HU or the amount of change in CT value from 10 HU to 200 HU strictly that the windmill artifact or the cone-beam artifact is being developed. Incidentally, the artifact determinator 27 (first determination unit 27-1) can suitably change the setting of the amount of change in CT value, based on the resolution, slice thickness or table velocity or the like at the photography. If the amount of change in CT value in the body-axis direction ranges from 3 HU to 300 HU as a result of various experiments, it can then be estimated that the artifacts are being developed.

Figure 7B:
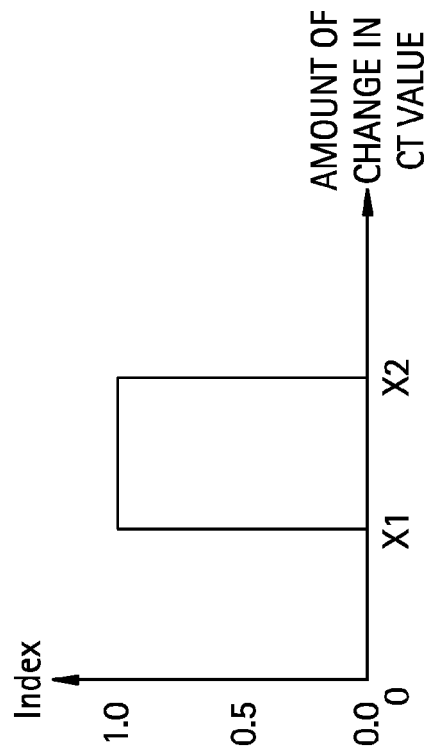

The index function of FIG. 7(b) is a function in which if the amount of change in CT value ranges from X1 to X3, then the index linearly changes from 0 to 1, if the amount of change in CT value ranges from X3 to X4, then the index remains at 1 as it is, and if the amount of change in CT value ranges from X4 to X2, then the index linearly changes from 1 to 0. Assume that, for example, X1 is 10 HU, X3 is 40 HU, X4 is 160 HU and X2 is 190 HU. According to the index function, the first determination unit 27-1 determines that if the amount of change in CT value ranges from 40 HU to 160 HU, then artifacts are developed.

Figure 7C:
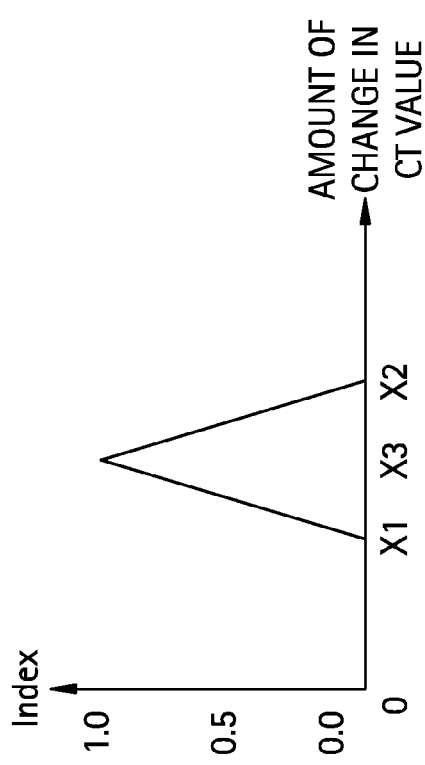

The index function of FIG. 7(c) is a function in which if the amount of change in CT value falls between X1 and X3, then the index changes into a curved form from 0 to 1, and if the amount of change in CT value falls between X3 and X2, then the index changes into a curved form from 1 to 0.

Figure 7D:
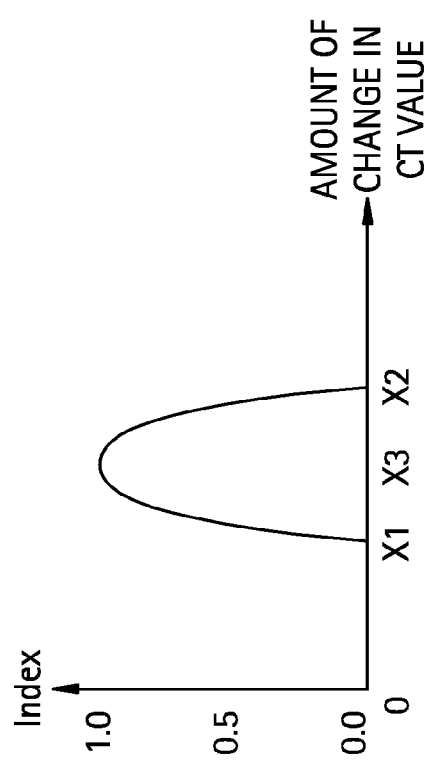

On the other hand, as to the index function of FIG. 7(d), if the amount of change in CT value falls between X1 and X2, then the index is 1 and 0 at other times. Therefore, if the amount of change in CT value is X1 or less or the amount of change in CT value is X2 or more, it then means that an image to be processed is used as a tomographic image as it is.

Although the index functions of (a) through (d) are shown in FIG. 7 as above, one function need not necessarily be used. It is possible to change the index function according to the position in the z direction. For example, the index function (a) may be used in a head region, the index function (c) may be used in a neck region, and the index function (d) may be used in a leg region. Even in the case of the flowchart shown in FIG. 4(b), the weighting factor gv may similarly be set depending upon the z-direction position.

Verification of Pixels in which Artifacts Exist.

If the amount of change in CT value of each target pixel ranges from 3 HU to 300 HU as described above, there is then a high probability of its target pixel being taken as an artifact. When there are, however, a blood vessel portion insufficient in the way of a blood vessel being extended or in contrasting of a contrast agent and a blood vessel portion sufficient therein, the amount of change in CT value of the target pixel might fall into a predetermined range due to an area change in other imaging condition. Therefore, whether the target pixel is as an artifact is determined using the artifact determinator 27 (second determination unit 27-2).

FIGS. 8 through 10 are diagrams for verifying whether each target pixel corresponds to an artifact, using a decision matrix MA-S or a decision matrix MA-T including pixels lying around a target pixel (x, y) of an nth sheet of tomographic image.

FIG. 8(a) is a diagram showing a windmill artifact, FIG. 8(b) is a diagram showing in enlarged form, an area surround by a frame b of FIG. 8(a), and FIG. 8(c) is a graph showing the amounts of change in CT values of two pixels in each of n−1th, nth and n+1th sheets of tomographic images.

As shown in FIG. 8(a), the windmill artifact is a feather-shaped image constituted of whitish and blackish pixels. In FIG. 8(b), the magnitude or size of the decision matrix MA-S is made up of 7*7=49 pixels. When the central target pixel p (x, y) of the decision matrix MA-S is of a whitish pixel, the amount of change in CT value is within a predetermined range as shown in FIG. 8(c). On the other hand, the amount of change in CT value of each peripheral pixel (x+i, y+j) in the decision matrix MA-S falls within a predetermined range. That is, the amounts of change in CT values of most pixels fall within the predetermined range, i.e., 3 HU to 300 HU. In each index of FIG. 7, the pixel is index=1. In such a case, the second determination unit 27-2 determines, when each pixel in the decision matrix MA-S is a first threshold value SU or more and the amount of change in CT value falls within the predetermined range, the target pixel p (x, y) as an artifact. For example, the artifact determinator 27 sets the first threshold value to, for example, 45 pixels or more, i.e., 90% or more of the 49 pixels in the decision matrix MA-S. Incidentally, this judgment criterion is suitably decided in consideration of a problematic artifact appearance form.

FIG. 9(a) is a diagram showing a blood vessel HB-B suddenly changed in the blood-vessel extending direction, and FIG. 9(b) is a graph showing the amounts of change in CT values of two pixels in each of n−1th, nth and n+1th sheets of tomographic images. In FIG. 9(a), the size or magnitude of a decision matrix MA-T is made up of 25 pixels. The shape of the decision matrix MA may be a polygon other than a quadrangle and can also be changed in match with an imaging region.

While the contrasted blood vessel HB-B shown in FIG. 9(a) extends in the body-axis direction (z direction), the blood vessel is suddenly bent in a different direction without extending straightforward in the z direction. The amount of change in CT value in the body-axis direction of the contrasted blood vessel HB-B falls within a predetermined range, i.e., 3 HU to 300 HU as shown in FIG. 9(b). The amounts of change in CT values of six pixels including the target pixel p (x, y) shown in FIG. 9(a) fall within a predetermined range. That is, at Step S181 of FIG. 4, the target pixel p (x, y) is determined as index>0 and estimated to be as an artifact. In a soft tissue other than the contrasted blood vessel HB-B, the amount of change in CT value is, for example, 2 HU or so and does not falls within the predetermined range. Therefore, the six pixels of the decision matrix MA-T comprised of the 25 pixels, i.e., 24 percents are estimated to be taken as an artifact. In such a case, the second determination unit 27-2 determines the target pixel p (x, y) not to be as an artifact because the first threshold value SU or more of each pixel in the decision matrix MA-T is not estimated to be an artifact.

FIG. 10(a) is a diagram showing a blood vessel HB-B that extends over an XY plane, and FIG. 10(b) is a graph showing the amounts of change in CT values of two pixels in each of n−1th, nth and n+1th sheets of tomographic images. In FIG. 10(a), the size of the decision matrix MA-S is constituted of 49 pixels.

FIG. 10(a) shows a case in which the contrasted blood vessel HB-B shown in FIG. 10(a) is not contrasted sufficiently and only part of the blood vessel is contrasted. Therefore, the amount of change in CT value in the body-axis direction of the contrasted blood vessel HB-B falls within a predetermined range, i.e., 3 HU to 300 HU as shown in FIG. 10(b). Therefore, the amounts of change in CT values of about 14 pixels containing a target pixel p (x, y) shown in FIG. 10(a) falls within a predetermined range. In a soft tissue other than the contrasted blood vessel HB-B, the amount of change in CT value is, for example, 2 HU or so and does not fall within the predetermined range. Therefore, the fourteen pixels of the decision matrix MA-S comprised of the 49 pixels, i.e., 29 percents are estimated to be as an artifact. In such a case, the second determination unit 27-2 determines the target pixel p (x, y) not to be an artifact because the first threshold value SU or more of each pixel in the decision matrix MA-S is not estimated to be an artifact.

The artifact determinator 27 (second determination unit 27-2) may set the size of the decision matrix MA-S to a decision matrix of 11*11 in the wake of enlarged or scaled-down representation of a tomographic image or may set it to a decision matrix of 3*3. The first threshold value SU may be changed to 80 to 95 percentages according to imaging conditions.

FIG. 11 is a flowchart for verifying an artifact-existing target pixel and is a flowchart showing Step S182 or S182' of FIG. 4 in detail.

At Step S821, the size of a decision matrix MT for the target pixel p is designated. An operator may set it using the input device 55. Alternately, a decision matrix MT made up of 25 pixels may automatically be set as a default.

At Step S822, the artifact determinator 27 (second determination unit 27-2) reads the amounts of change in CT values of all pixels in the decision matrix MT measured at Step S172 of FIG. 4. Although the three sheets of tomographic images in the body-axis direction have been shown in FIGS. 8 through 10, any sheets of tomographic images may be used if 2n+1 sheets of tomographic images are taken.

At Step S823, it is determined whether each pixel in which the amount of change in CT value falls in the predetermined range within the decision matrix MT, i.e., each pixel estimated to be as the artifact is the first threshold value SU or more.

When the pixel estimated to be as the artifact exists as the first threshold value SU or more, the artifact determinator 27 proceeds to Step S824. The second determination unit 27-2 determines that the target pixel p is as the artifact. When the pixel estimated to be as the artifact is the first threshold value Su or less, the artifact determinator proceeds to Step S825, where it is overturned to estimate that the target pixel p has been taken as the artifact at Step S181 of FIG. 4, and the target pixel is determined to be a pixel that does not correspond to the artifact.

Although the amount of change in CT value of the target pixel p happens to fall into the predetermined range depending upon regions, the target pixel p is not regarded as being the artifact unless the majority of decision matrices MT is judged to be an artifact.

Specifying Tomographic Images in which Artifacts Exist.

In the following embodiment, there is provided a technique or method for further enhancing specifying of an area with artifacts developed therein by the artifact determinator 27 (third determination unit 27-3).

FIG. 12 is a diagram showing tomographic images prior to being subjected to an artifact reduction process, of the head of a subject, and reconstruction areas P. Many windmill artifacts exist in the upper stage tomographic image D3-A shown in FIG. 12(A1), and the windmill artifacts almost remain nonexistent in the lower stage tomographic image D3-B shown in FIG. 12(B1). The reconstruction area P shown in FIG. 12 is a square area of 512×512 pixels, which is parallel to an xy plane. As a result of determination of indexes about the tomographic image D3-A and the tomographic image D3-B, pixels brought to index>0 are filled in. In the reconstruction area P shown in FIG. 12(A2), the artifact ratio obtained by dividing the number of pixels at index>0 by the entire number of pixels is 0.12. In the reconstruction area P shown in FIG. 12(B2), the artifact ratio obtained by dividing the number of pixels at index>0 by the entire number of pixels is 0.30. This calculation is performed by the artifact ratio calculator 29 shown in FIG. 1.

When the processing of the equation (1) or (2) is effected on each pixel of index>0 regardless of the fact that the windmill artifact remains almost non-existent in the tomographic image D3-B, the resolution in the z direction is degraded. Therefore, the artifact ratio calculator 29 checks for the artifact ratio corresponding to the ratio indicative of how pixels estimated to be index>0, i.e., to have developed the artifacts, of the entire pixels in the reconstruction area P are taken up or occupied. When the artifact ratio is larger than a predetermined second threshold value SH, the artifact determinator 27 (third determination unit 27-3) effects the processing of the equation (1) or (2) on the tomographic image D3. That is, the third determination unit 27-3 makes the decision that the artifact is recognized as developed, more stringent.

FIG. 13 shows a flowchart for performing an artifact reduction process after examinations of the artifact ratios. The flowchart shown in FIG. 13 is a flowchart showing Step S183 or S183' of FIG. 4 in detail.

At Step S831, the artifact ratio calculator 29 calculates an artifact ratio. As to the artifact ratio, the ratio between pixels of index>0, of all pixels (512×512) is calculated. Since the index is not used at Step S183', the ratio at which the amount of change in CT value falls within a predetermined range, is calculated.

Incidentally, an area for the subject HB is specified in place of all pixels, and the ratio between pixels of index>0 may be calculated in the number of pixels in that area. In place of the ratio between the pixels of index>0, the ratio between points or spots of index=1, index>0.7 or index>0.5 may be calculated. The following description will be made of, as the artifact ratio, the ratio between the pixels of index>0, of all the pixels (512×512).

At Step S832, the third determination unit 27-3 determines whether the artifact ratio is larger than the second threshold value SH. For example, the artifact ratio=0.07 is used as the second threshold value SH. If the artifact ratio of a target tomographic image D3 is larger than the second threshold value SH, then the third determination unit proceeds to Step S833. If this artifact ratio is smaller than the second threshold value SH, then the third determination unit proceeds to Step S834.

At Step S833, the third determination unit 27-3 determines that a tomographic image n contains an artifact. Therefore, each pixel judged to be the artifact within the tomographic image n proceeds to Step S191 of FIG. 4, and a pixel p (x, y, z) to be processed is image-processed based on the corresponding index value to determine a pixel p' (x, y, z) subsequent to its processing.

On the other hand, at Step S834, the third determination unit 27-3 determines that all the pixels contained in the target tomographic image n are not taken as artifacts. This is because although there is a possibility that the pixels of index>0 will cause the artifacts in the reconstruction area P, the artifacts are considered to be inconspicuous since the pixels of index>0 1 are low in number in the entire reconstruction area P, and such image processing as to degrade the resolution in the body-axis direction is undesirable.

Figure 14:
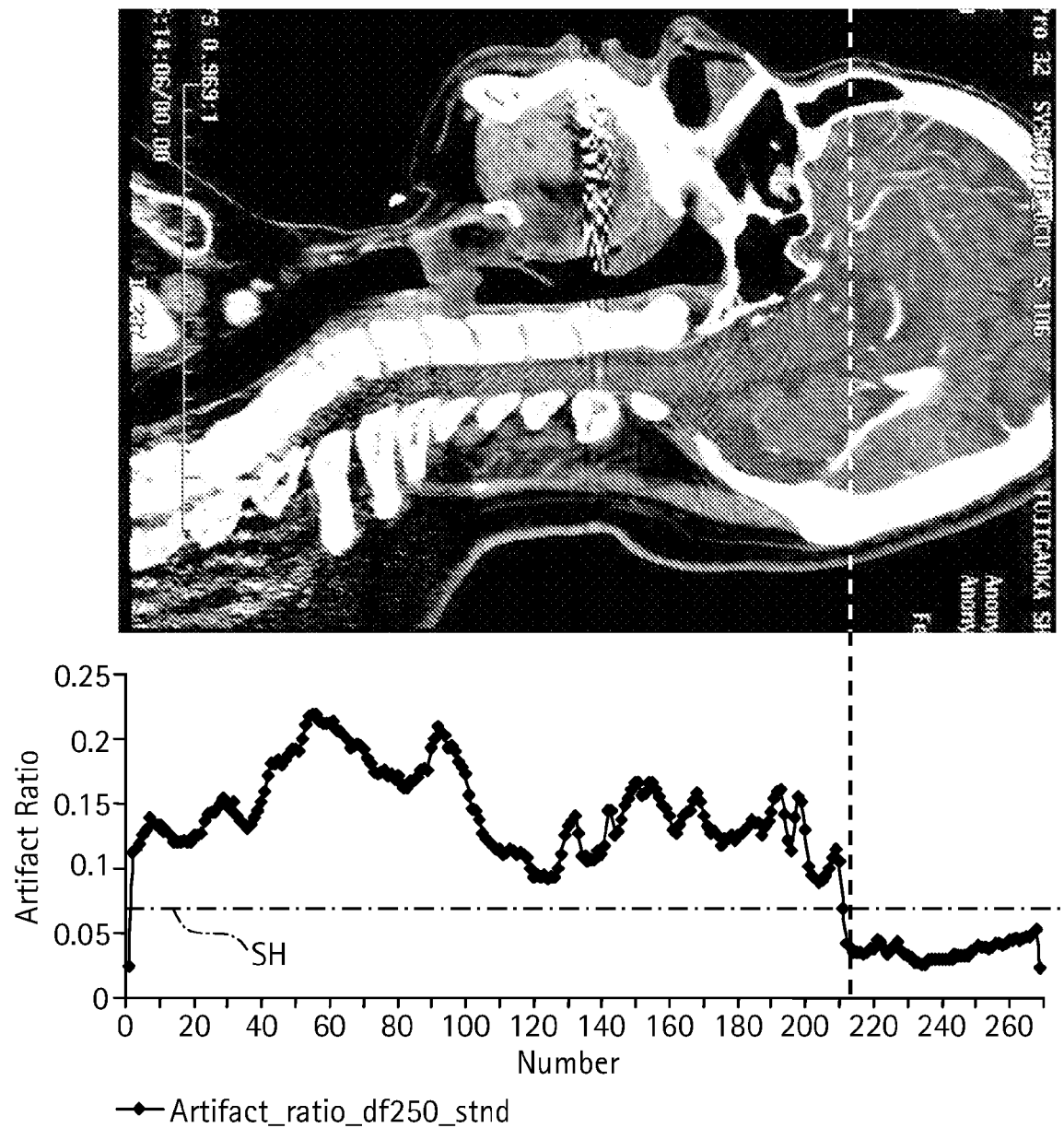
FIG. 14 is a cross-sectional view in a body-axis direction from the chest of a subject HB to the head thereof, and artifact ratios.

FIG. 14 is a cross-sectional view in a body-axis direction from the chest of a subject HB to the head thereof at its upper stage, and is a diagram showing the relationship between artifact ratios and the numbers of tomographic images n arranged in the body-axis direction at its lower stage.

Looking at the relationship between the artifact ratios and the body-axis direction, the artifact ratio of the chest to the neighborhood (indicated by a white dotted line in FIG. 14) of the eyes or eyebrows of the head ranges from 0.9 to 2.2 or so. In the tomographic image D3 (x, y, z) prior to execution of the artifact reduction process of the present embodiment, the artifact ratio between the neighborhood of the eyes or eyebrows and the top of head ranges from 0.3 to 0.5 or so. As understandable from FIG. 14, the more the shape of a structure such as a bone becomes complex, the more the artifacts are easy to occur. When the shape of the bone or the like lying in the vicinity of the top of head is simple in reverse, the artifacts are hard to occur. In FIG. 14, the artifact ratio=0.07 is defined as the threshold value. Therefore, according to the flowchart of FIG. 13, the image processing of the equation 1 or the like is effected on the tomographic image D3 in the vicinity of the chest to the neighborhood of the eyes or eyebrows of the head. On the other hand, the image processing of the equation 1 or the like is not effected on part of the tomographic image D3 between the neighborhood of the eyes or eyebrows and the top of head even though the pixels of index>0 exist.

Incidentally, the image reconstructing method according to the present embodiment may be a three-dimensional image reconstructing method based on the Feldkamp method known to date. Further, another three-dimensional image reconstructing method may be adopted. Alternatively, two-dimensional image reconstruction may be adopted. Image quality determined as each region varies according to diagnostic applications, the preferences of an operator, etc. and exists in a wide variety of forms. Therefore, the operator may set the setting of an imaging condition most suitable for each region in advance.

Although the amount of change in CT value has been explained using the difference between the maximum and minimum CT values of one slice or plural slices in the neighborhood of the pixel p (x1, y1, z1) to be processed, it may be processed using the average amount of change in CT value obtained by dividing the difference between the maximum CT value and the minimum CT value by the number of slices.

Although the present embodiment has shown the example in which in-relocation is judged though the artifacts can be generated according to the amount of change in CT value in the body-axis direction between the plural tomographic images, it can also be determined using another method.

The first threshold value SU used in the artifact determinator (second determination unit 27-2) of the present embodiment and the second threshold value SH employed in the third determination unit 27-3 are not limited to those employed in the present embodiment. They can suitably be changed in consideration of a problematic artifact appearance form or the like.

In the present embodiment, the processing of judgement by the third determination unit 27-3 has been effected on each pixel judged as being the artifact by the artifact determinator after the processing of determination by the second determination unit 27-2. However, the processing of judgement by the second determination unit 27-2 may be effected on each pixel judged as being the artifact by the third determination unit 27-3.

The present embodiment is not limited to the specific scan form in particular. That is, similar effects can be brought about even in the case of an axial scan, a cine scan, a helical scan, a variable pith helical scan and a helical shuttle scan. The present embodiment is not limited to the tilt or gradient of the gantry 100. That is, similar effects can be brought about even in the case of a so-called tilt scan at which the gantry 100 is tilted. The present embodiment can be applied even to cardiac image reconstruction which image-reconstructs each image in sync with a biological signal, particularly, a cardiac signal.

Although the present embodiment has been described on the basis of the medical X-ray CT apparatus 10, it can be made available even to an X-ray CT-PET apparatus utilized in combination with an industrial X-ray CT apparatus or another apparatus, an X-ray CT-SPECT apparatus utilized in combination therewith, etc.

The invention claimed is:

1. An X-ray tomography apparatus comprising:
a scan device configured to direct X-rays through a subject while at least one of a gantry and a table is moved along a body-axis direction of the subject to create projection data of the subject;
a first artifact determination unit configured to identify at least one pixel of a plurality of pixels as artifact based on a change in a computed tomography (CT) value between a first tomographic image of a plurality of tomographic images and a second tomographic image of the plurality of tomographic images in the body-axis direction, the plurality of tomographic images obtained by backprojecting the projection data;
a second artifact determination unit configured to set a decision pixel area containing the at least one pixel identified as artifact as a target pixel and areas lying around the target pixel in at least one tomographic image of the plurality of tomographic images, and to re-identify the target pixel as artifact based on a comparison to a first predetermined reference; and
an artifact reduction unit configured to perform an image process for reducing artifact on the at least one pixel that is re-identified as artifact.

2. The X-ray tomography apparatus according to claim 1, further comprising:
an artifact ratio calculating device configured to calculate a ratio of a number of pixels identified as artifact in the at least one tomographic image and a total number of pixels in the at least one tomographic image; and
a third artifact determination unit configured to re-identify the at least one pixel as artifact when the ratio is larger than a predetermined threshold value.

3. The X-ray tomography apparatus according to claim 1, wherein the artifact reduction unit is configured to multiply a plurality of pixels in the at least one tomographic image in the body-axis direction by at least one weighting factor, add results of the multiplication, and reduce artifact of the target pixel in the at least one tomographic image.

4. The X-ray tomography apparatus according to claim 3, wherein the artifact reduction unit is configured to change the at least one weighting factor based on a number of decision pixel areas in the body-axis direction.

5. The X-ray tomography apparatus according to claim 1, wherein the decision pixel area is shaped in the form of a quadrangle or a polygon.

6. The X-ray tomography apparatus according to claim 1, wherein the second artifact determination unit is configured to change a number of pixels constituting the decision pixel area according to an enlarged display of each of the plurality of tomographic images and a reduced display of each of the plurality of tomographic images.

7. The X-ray tomography apparatus according to claim 6, wherein the first predetermined reference at the second artifact determination unit is variable.

8. The X-ray tomography apparatus according to claim 1, wherein the first artifact determining unit is further configured to identify the at least one pixel as artifact based on a comparison to a second predetermined reference, and wherein the second predetermined reference is variable.

9. The X-ray tomography apparatus according to claim 8, wherein the first predetermined reference at the second artifact determination unit is variable.

10. The X-ray tomography apparatus according to claim 1, wherein the first predetermined reference at the second artifact determination unit is variable.

11. A method of reducing artifacts in a tomographic image, comprising:
transmitting X-rays to a subject while at least one of a gantry and a table is moved along a body-axis direction of the subject to generate projection data;
obtaining a plurality of tomographic images by backprojecting the projection data;
determining whether each of a plurality of pixels contained in each tomographic image of the plurality of tomographic images is artifact based on an amount of change in a computed tomography (CT) value in the body-axis direction between a first tomographic image of the plurality of tomographic images and a second tomographic image of the plurality of tomographic images;
setting a decision pixel area containing at least one pixel of the plurality pixels identified as artifact as a target pixel and areas lying around the target pixel, and re-determining whether the target pixel is artifact based on a comparison to a first predetermined reference; and
performing an image process to reduce artifact on each pixel of the plurality of pixels determined to be artifact.

12. The method according to claim 11, further comprising:
calculating a ratio of a number of pixels determined to be artifact in at least one of the plurality of tomographic images and a total number of pixels in the at least one of the plurality of tomographic images; and
re-determining whether each of the plurality of pixels is artifact when the ratio is larger than a predetermined threshold value.

13. The method according to claim 11, further comprising performing a beam hardening correction on the projection data of the subject, wherein obtaining a plurality of tomographic images comprises backprojecting the corrected projection data.

14. The method according to claim 11, wherein performing an image process comprises multiplying the plurality of pixels in the body-axis direction by a plurality of weighting factors, adding results of the multiplication and reducing artifact of each target pixel in each of the plurality of tomographic images.

15. The method according to claim 11, further comprising changing a number of pixels constituting the decision pixel area according to an enlarged display of each of the plurality of tomographic images and a reduced display of each of the plurality of tomographic images.

16. The method according to claim 11, wherein determining whether each of a plurality of pixels is artifact comprises comparing each of the plurality of pixels to a second predetermined reference, wherein the second predetermined reference is variable.

17. The method according to claim 11, wherein re-determining whether the target pixel is artifact comprises comparing the target pixel to the first predetermined reference, wherein the first predetermined reference is variable.

* * * * *